United States Patent [19]
Han et al.

[11] Patent Number: 6,113,909
[45] Date of Patent: Sep. 5, 2000

[54] PHARMACEUTICAL COMPOSITION CONTAINING A MIXED EXTRACT OF *PHELLODENDRON AMURENSE* RUPRECHT CORTEX AND *PATRINIA SCABIOSAEFOLIA* FISCH. FOR TREATMENT OF HEPATITIS C

[75] Inventors: Young Bok Han, Seoul; Eun Kyung Hong, Goonpo; Young Shin Chung, Seoul; Bo Im Yoo, Seoul; Sang Geon Kim, Seoul; Kyung Yung Lee, Seoul, all of Rep. of Korea

[73] Assignees: Young Hee Kim, Santa Monica, Calif.; Young Bok Han, Seoul, Rep. of Korea

[21] Appl. No.: 09/284,022

[22] PCT Filed: Jul. 15, 1998

[86] PCT No.: PCT/KR98/00214

§ 371 Date: Apr. 6, 1999

§ 102(e) Date: Apr. 6, 1999

[87] PCT Pub. No.: WO99/07399

PCT Pub. Date: Feb. 18, 1999

[30] Foreign Application Priority Data

Aug. 7, 1997 [KR] Rep. of Korea .................. 97-37815

[51] Int. Cl.[7] .................................................. A61K 35/78
[52] U.S. Cl. ............................................................ 424/195.1
[58] Field of Search ............................................ 424/195.1

[56] References Cited

U.S. PATENT DOCUMENTS 5,244,662 9/1993 Han et al. .

OTHER PUBLICATIONS

Japanese Abstract: JP 01–272581A, vol. 14, No. 37, 1990.
Japanese Abstract: JP 01–224317A, vol. 13, No. 549, 1989.
Derwent Publications Ltd. AN 97–527439, CN 1 127 125.

*Primary Examiner*—James H. Reamer
*Attorney, Agent, or Firm*—Birch, Stewart, Kolasch & Birch, LLP

[57] ABSTRACT

The present invention relates to a pharmaceutical composition for the treatment of hepatitis C which comprises a mixed extract, particularly a mixed aqueous extract or a mixed alcohol extract, of *Phellodendron amurense* RUPRECHT cortex and *Patrinia scabiosaefolia* FISCH. as an active ingredient. The mixed extract according to the present invention exhibits an anti-viral activity for hepatitis C and help prevents hepatic cirrhosis orginated from hepatitis C, and further treats hepatitis and hepatic cirrhosis by potentiating the immunological function to inhibit the proliferation of hepatitis C virus and stimulating the proliferation of T helper cells to increase the host immune system. Furthermore, the mixed extract of the present invention is a mixed extract of natural plants characterized in that it does not exhibit any side effects nor drug resistance, and its activity is maintained even when used for a long period.

20 Claims, 20 Drawing Sheets

File Name: Patrinia

Created: 10:47 98/06/18
Data: Original

Measure Mode: Abs.
Scan Speed: Fast
Slit Width: 2.0
Sampling Interval: 0.5

Point Pick

| No. | Wavelength (nm.) | Abs. |
|---|---|---|
| 1 | 201.50 | 2.530 |
| 2 | 208.50 | 1.938 |
| 3 | 225.00 | 1.081 |
| 4 | 260.50 | 0.506 |
| 5 | 282.00 | 0.581 |
| 6 | 302.50 | 0.492 |
| 7 | 321.00 | 0.461 |
| 8 | 353.50 | 0.192 |
| 9 | 374.50 | 0.089 |
| 10 | 389.50 | 0.063 |
| 11 | 413.00 | 0.043 |
| 12 | 431.50 | 0.034 |
| 13 | 461.50 | 0.025 |
| 14 | 559.00 | 0.013 |
| 15 | 659.50 | 0.006 |

File Name: Phellodendron

Created: 10:49 98/06/18
Data: Original

Measure Mode: Abs.
Scan Speed: Fast
Slit Width: 2.0
Sampling Interval: 0.5

| No. | Point Pick Wavelength (nm.) | Abs. |
|---|---|---|
| 1 | 201.50 | 2.617 |
| 2 | 218.50 | 1.551 |
| 3 | 257.00 | 0.575 |
| 4 | 279.00 | 0.655 |
| 5 | 300.00 | 0.509 |
| 6 | 324.00 | 0.551 |
| 7 | 347.50 | 0.341 |
| 8 | 369.50 | 0.093 |
| 9 | 384.50 | 0.061 |
| 10 | 411.50 | 0.047 |
| 11 | 426.50 | 0.042 |
| 12 | 438.50 | 0.034 |
| 13 | 453.50 | 0.022 |
| 14 | 542.50 | 0.005 |
| 15 | 601.00 | 0.003 |

File Name: the extract of the present Invention
Created: 10:51 98/06/18
Data: Original Measure Mode: Abs.
Scan Speed: Fast
Slit Width: 2.0
Sampling Interval: 0.5

Point Pick

| No. | Wavelength (nm.) | Abs. |
|---|---|---|
| 1 | 201.50 | 2.398 |
| 2 | 210.00 | 1.722 |
| 3 | 213.50 | 1.491 |
| 4 | 245.50 | 0.594 |
| 5 | 260.50 | 0.467 |
| 6 | 280.50 | 0.554 |
| 7 | 299.00 | 0.473 |
| 8 | 310.50 | 0.457 |
| 9 | 326.00 | 0.437 |
| 10 | 354.50 | 0.167 |
| 11 | 366.00 | 0.091 |
| 12 | 379.50 | 0.059 |
| 13 | 401.50 | 0.040 |
| 14 | 448.50 | 0.023 |
| 15 | 535.50 | 0.010 |

|   | Peak Start (minutes) | Peak End (minutes) | Retention Time (minutes) | Peak Area | Peak Height |
|---|---|---|---|---|---|
| 1 | 9.708 | 10.875 | 10.358 | 1012701 | 38083 |
| 2 | 10.875 | 12.000 | 11.325 | 965878 | 28882 |
| 3 | 12.000 | 13.125 | 12.567 | 997443 | 34856 |
| 4 | 13.125 | 14.425 | 13.667 | 931997 | 32373 |
| 5 | 15.325 | 17.358 | 16.833 | 1025778 | 23800 |
| 6 | 17.358 | 19.133 | 17.808 | 942416 | 25264 |
|   |   |   |   | 5876214 | 183258 |

Sample: STANDARD2 0.6ml  Channel: RID  Filename: SUGAR-54
Acquired: 27-SEP-95 11:46  Method: C:₩:MAX₩DATA₩SUGAR
Operator: sky  Inj vol: 20.00

ECTOR: RID

| | Peak Start (minutes) | Peak End (minutes) | Retention Time (minutes) | Peak Area | Peak Height |
|---|---|---|---|---|---|
| 1 | 9.208 | 13.450 | 10.992 | 943664 | 26539 |
| 2 | 13.450 | 17.467 | 14.750 | 904934 | 29786 |
| | | | | 1848599 | 56325 |

| | Peak Start (minutes) | Peak End (minutes) | Retention Time (minutes) | Peak Area | Peak Height |
|---|---|---|---|---|---|
| 1 | 5.975 | 6.783 | 6.425 | 62698 | 2229 |
| 2 | 6.783 | 7.508 | 7.100 | 76146 | 4581 |
| 3 | 8.000 | 8.542 | 8.450 | 9014 | 803 |
| 4 | 9.258 | 10.025 | 9.892 | 142564 | 5936 |
| 5 | 10.025 | 10.967 | 10.350 | 386830 | 13708 |
| 6 | 10.967 | 11.775 | 11.375 | 15952 | 566 |
| 7 | 11.867 | 13.217 | 12.558 | 311634 | 10817 |
| 8 | 13.350 | 14.158 | 13.667 | 26295 | 1099 |
| 9 | 14.158 | 15.325 | 14.742 | 15006 | 376 |
| 10 | 17.125 | 18.567 | 17.842 | 181245 | 5147 |
| 11 | 19.775 | 20.583 | 20.175 | 7884 | 471 |
| 12 | 21.758 | 22.925 | 22.250 | 4651 | 173 |
| | | | | 1239919 | 45909 |

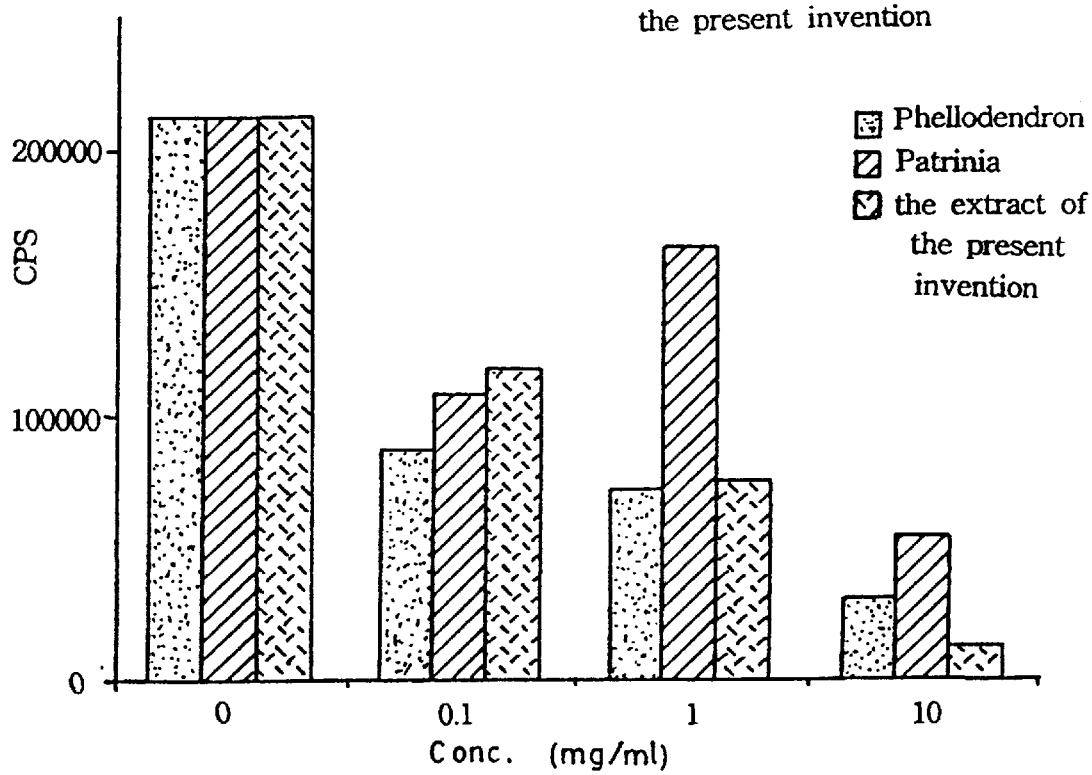
FIG. 20 Antioxidant activity of the extract of the present invention

PHARMACEUTICAL COMPOSITION CONTAINING A MIXED EXTRACT OF *PHELLODENDRON AMURENSE* RUPRECHT CORTEX AND *PATRINIA SCABIOSAEFOLIA* FISCH. FOR TREATMENT OF HEPATITIS C

This application is the national phase under 35 U.S.C. §371 of PCT International Application No. PCT/KP98/00214 which has an International filing date of Jul. 15, 1998, which designated the United States of America.

TECHNICAL FIELD

The present invention relates to a pharmaceutical composition for treatment of hepatitis C which contains a mixed extract of *Phellodendron amurense* RUPRECHT cortex and *Patrinia scabiosaefolia* FISCH. as an active ingredient. More specifically, the present invention relates to a pharmaceutical composition which contains a mixed extract obtained from the mixture of *Phellodendron amurense* RUPRECHT cortex and *Patrinia scabiosaefolia* FISCH. in water or alcohol extraction, as an active ingredient, which can be used effectively for the treatment of hepatitis C and hepatic cirrhosis originated from hepatitis C due to its anti-viral activity against hepatitis C virus and, at the same time, its ability to retrieve the damaged T helper cells to reinforce the host immune system.

BACKGROUND ART

Chronic hepatitis C is a disease characterized in that the infection of hepatitis C viruses (HCV) continuously induces inflammation in liver centering around the area of portal vein, and advances to hepatic cirrhosis or primary hepatocellular carcinoma. Contrary to hepatitis A or B, about 90% of hepatitis C shows abnormal GPT (glutamic-pyruvic transaminase) level, even at the primary infection, and develops into chronic illness. Recently, it is reported that hepatitis C virus may directly participate in the induction of hepatocellular carcinoma [see, Sakamuro, Furukawa and Takegami, J. Virol. 69: 3893–3896, 1995; Ray, Logging, Meyer and Ray, J. Virol. 70: 4438–4443, 1996]. In addition, it is also reported that hepatitis C virus is detected in 30% of patients with hepatocellular carcinoma in western countries [see, Mangia, Vallari and Bisceglie, J. Med. Virol. 43, 125–128, 1994].

According to the development of HCV antibody (C100-3 antibody) detection system by Chiron Inc. (U.S.A.) in 1988, it has been revealed that the majority of non-A, non-B hepatitis are caused by hepatitis C virus. In Japan, the screening assay using antibody detection system has allowed to demonstrate that hepatitis C virus is detected in 70% of patients suffering from non-A, non-B hepatitis and in 90% or more of hepatoma patients.

In 1989, the nature of hepatitis C virus was first identified by separating a part of virus gene from the serum of chimpanzee suffering from non-A, non-B hepatitis. That is, hepatitis C virus belongs to Flaviviridae having 9.5 kb positive(+)-stranded RNA as a gene, and synthesizes viral polypeptide precursor in host cells. The precursor protein is transformed into structural proteins (core, E1, E2), which are directly comprised to make up the viral structure, and non-structural proteins (NS2, NS3, NS4A, NS4B, NS5A, NS5B) having enzymatic activities after the post-translational modification by the signal peptidase of a host, and by metalloprotease and serine protease produced from hepatitis C virus. Particularly, numerous variants can be produced due to the presence of two hypervariable regions (HVR1 and HVR2) on the 5' end of E2 gene.

Although the mechanism related to the progression from chronic hepatitis C to hepatocellular carcinoma has not been yet established, chronic inflammation and the intensity of inflammation may be closely related. That is, although the host immune system produces neutralizing antibody against hepatitis C virus, the neutralizing antibody affects only the limited types of viruses, and the variants resistant to the neutralizing antibody are produced quickly (genetic mutation at high rate). In spite of the presence of the neutralizing antibody, the variants may continuously induce inflammation in the host (immune escape). Further, the regeneration ability of host liver cells from the continuous infectious damages may cause tumorigenesis. Recently, it has been reported that double strand RNA-dependent protein kinase R (PKR) of host cells can phosphorylate eIF-2a to stimulate apoptosis of virus. However, hepatitis C virus produces proteins capable of inactivating PKR. For example, it may be explained that the resistance of hepatitis C virus to the administration of interferon is caused by inactivation of PKR by the variants of hepatitis C virus. Hence, the presence of variants is an obstacle to the production of vaccine against hepatitis C virus.

Due to such characteristics of hepatitis C virus, many drugs currently being, used as a therapeutic agent for the treatment of hepatitis C cannot provide a sufficient therapeutic effect. The effects of interferon may prevent the incidence of hepatic cirrhosis and hepatocellular carcinoma originated from hepatitis C, rather than actually reduce hepatitis C virus. Further, clinical studies report numerous adverse effects of interferon. Hence, there is a prevalent course for studies and researches in the scientific community to find and develop the inhibitors of hepatitis C virus protease for the treatment of hepatitis C.

The present inventors have extensively studied to find out the material which resolves the problems involved in the prior therapeutic agents used for treatment of hepatitis C such as interferon, and which has an immunopotentiating activity as well as an anti-viral activity against hepatitis C virus for an effective treatment. Particularly, the inventors have studied various natural medicinal plants as the subject their research. As a result, it has been concluded that among numerous natural plants the mixed extract obtained from the mixture of *Phellodendron amurense* RUPRECHT cortex and *Patrinia scabiosaefolia* FISCH. can accomplish the purpose of the present invention as mentioned above.

DISCLOSURE OF THE INVENTION

Accordingly, the purpose of the present invention is to develop and provide a pharmaceutical composition for the treatment of hepatitis C which contains a mixed extract of *Phellodendron amurense* RUPRECHT cortex (Rutaceae) and *Patrinia scabiosaefolia* FISCH. (Valerianaceae) as an active ingredient.

More specifically, the present invention relates to a pharmaceutical composition for the treatment of hepatitis C which comprises, as an active ingredient, a mixed aqueous or alcoholic extract of *Phellodendron amurense* RUPRECHT cortex and *Patrinia scabiosaefolia* FISCH.

BRIEF DESCRIPTION OF DRAWINGS

For a thorough understanding of the nature and objects of the invention, reference should be made to the following detailed description taken in connection with the accompanying drawings in which:

FIG. 19 is a photograph showing the effects of the mixed aqueous extract of *Phellodendron amurense* RUPRECHT cortex and *Patrinia scabiosaefolia* FISCH. according to the present invention on liver, kidney and heart (tissue morphology) of mouse [dose 15 g/kg, H&E staining.

FIG. 20 represents anti-oxidant activity of the mixed aqueous extract of the present invention.

BEST MODE FOR CARRYING OUT THE INVENTION

Figure 1:
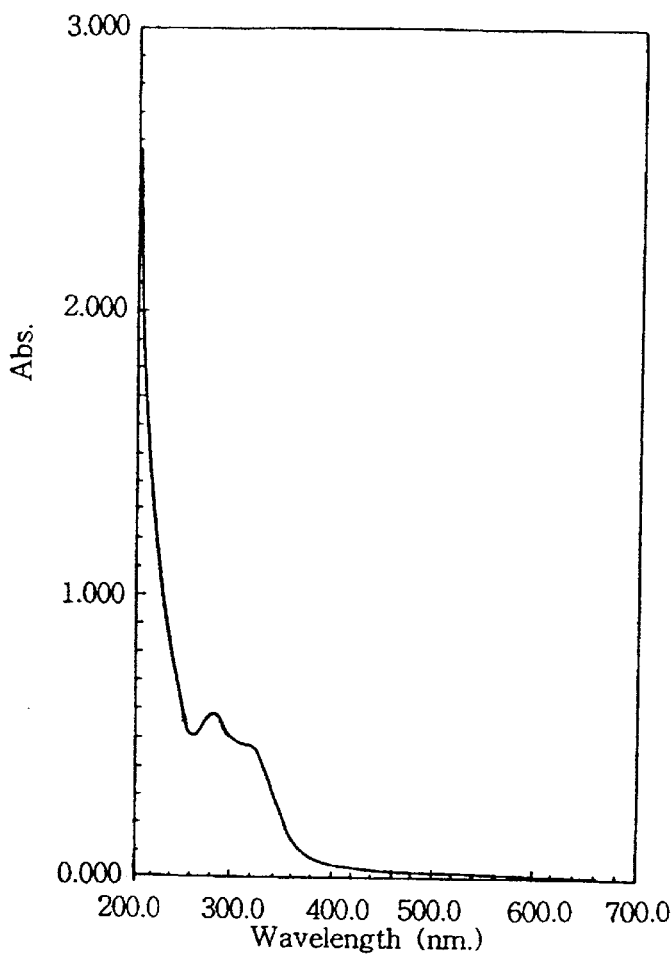
FIG. 1 represents UV scanning profile of an aqueous extract obtained from *Patrinia scabiosaefolia* FISCH.

Hereinafter, the present invention will be more specifically explained.

The present invention relates to a pharmaceutical composition for the treatment of hepatitis C which comprises as an active ingredient a mixed extract, specifically mixed aqueous or alcoholic extract, obtained from a mixture of *Phellodendron amurense* RUPRECHT cortex and *Patrinia scabiosaefolia* FISCH. Particularly, the composition of the present invention exhibits a direct anti-viral activity against hepatitis C virus in chronic hepatitis C and in the primary stage of hepatic cirrhosis. At the same time, this composition reduces inflammation and potentiates the activity of T helper cells involved in the host immune system. Accordingly, the composition of the present invention can be used effectively for the treatment of hepatitis C or hepatic cirrhosis originated therefrom through a direct intervention and preventive mechanisms.

Furthermore, as demonstrated by the following, experiments, the mixed extract of the present invention has a strong therapeutic activity against hepatitis C while exhibiting extremely low toxicity, and does not produce any adverse effects in human drug resistance. Thus, the composition of the present invention is ideal, in terms of safety and its use in long-term treatment.

As one of the plants used for preparing the mixed extract of the present invention, *Patrinia scabiosaefolia* FISCH. (Valerianaceae) belongs to the same class with *Patrinia villosa* JUSS., *Patrinia sibirica* JUSS., etc. and is a perennial herbal plant native in the fields and mountains of all temperate regions, including Korea. In Chinese medicine, it has long been used as an anti-inflammatory agent for the treatment of ophthalmic disease, Streptococcus pyogenic infection, edema, hysterorrhea, etc. In addition, the following activities have been reported:

a) an anti-tumor activity (e.g. uterine cancer, esophageal cancer, gastric cancer, intestinal cancer, etc.) of the extract in hot water;

b) anti-bacterial activity against Staphylococcus aureus, Streptococcus, etc.;

c) an ability to stimulate the regeneration of damaged liver cells resulting in the prevention of degeneration of liver cells;

d) an improvement of the blood circulation in portal veins to stimulate the regeneration of liver cells;

e) an effect of stabilizing central nervous system;

f) a potent analgesic activity;

g) anti-hypertensive and diuretic activity.

*Patrinia scabiosaefolia* FISCH., in its roots, contains essential oils, various saponins, carbohydrates and a trace amount of alkaloids such as cumarin. In the cortex layer of the root, acetic acid, formic acid, valeric acid, etc., and alkaloids such as chatinine and valerianine are found. Among these components, valeric acid has been known as very potent analgesic compound. In the dry seeds, 19.4–19.9% of proteins and 30–34.4% of fats are contained. However, specific scientific studies of the active ingredients included in *Patrinia scabiosaefolia* FISCH. and their pharmacological activities have not yet been made. Moreover, the result of study demonstrating the anti-HCV activity of any extracts or ingredients of *Patrinia scabiosaefolia* FISCH. has never been reported.

As another plant used for preparing the extract of the present invention, *Phellodendron amurense* RUPRECHT cortex is a cortex layer of the stem of *Phellodendron*

*amurense* RUPRECHT (Rutaceae) native in Korea, Japan, China, etc. The variants of *Phellodendron amurense* RUPRECHT include *Phellodendron amurense* var. *latifoliolatum* NAKAI, var. *japonicum* OHWI, *P. insulare* NAKAI, *P. molle* NAKAI, *P. sachalinense* Sarg., etc. *Phellodendron amurense* RUPRECHT cortex contains 1.5–4.5% of yellow or yellowish-brown pigments and numerous alkaloid components. The major alkaloid component is berberine. In addition, palmatine, magnoflorine, guanidine, jateorrizine, phellodendrine, candicine, menisperine, etc. are also contained. Further, it has been known that obakunone, obakulactone, β-sitosterol, etc. are contained as the bitter components. These components have a potent antibacterial activity, anti-hypertensive activity, central nervous system suppressive activity, acetylcholinergic activity and anti-inflammatory activity. This plant has been used for the treatment of bone diseases and jaundice in Chinese medicine. In addition, *Phellodendron amurense* RUPRECHT cortex also contains effective components for typhoid fever and cholera and is useful therapeutic materials for gastric and intestinal disorders. Meanwhile, the cortex of *Phellodendron amurense* RUPRECHT has been used for the treatment of gastroenteritis, aneilema, jundice, etc. as a bitter stomachic, an agent for intestinal flora and an anti-inflammatory astringent. However, it has never been reported that *Phellodendron amurense* RUPRECHT cortex includes any compounds to inhibit the proliferation of hepatitis C virus, and to reinforce the immune system by retrieving the damaged T helper cells.

In the present invention, it has been identified through numerous experiments that the mixed extract, obtained from the mixture of *Phellodendron amurense* RUPRECHT cortex and *Patrinia scabiosaefolia* FISCH. in water or an alcohol extraction, has an anti-viral activity against hepatitis C virus and an effect on the immune function by stimulating the proliferation of T helper cells. It also exhibits a synergistic pharmacological effect which is far superior than any extracts obtained from the extraction of *Phellodendron amurense* RUPRECHT cortex or *Patrinia scabiosaefolia* FISCH. alone. Accomplishment of the present invention is supported by the basis of such findings.

The mixed extract of *Phellodendron amurense* RUPRECHT cortex and *Patrinia scabiosaefolia* FISCH., which is used as an active substance according to the present invention, can be obtained according to the following method.

Specifically, the mixed aqueous extract of *Patrinia scabiosaefolia* FISCH. and *Phellodendron amurense* RUPRECHT cortex can be obtained from the mixture of two plants by extracting with water, filtering the extracted solution under high pressure, removing the precipitate of coagulated proteins after centrifugation, from supernatant and lyophilizing the aqueous layer to produce a powdery residue (the mixed aqueous extract).

In addition, the mixed alcoholic extract of *Patrinia scabiosaefolia* FISCH. and *Phellodendron amurense* RUPRECHT cortex can be obtained from the mixture of two plants by extracting with alcohol, preferably having 1 to 4 carbon atoms, for example, methanol, ethanol, etc., evaporating the solvent, adding water to the residue, heating and filtering the mixture, removing the organic solvent soluble materials from the filtrate using organic solvent and lyophilizing the resulting aqueous layer (the mixed alcoholic extract).

In these processes, *Phellodendron amurense* RUPRECHT cortex and *Patrinia scabiosaefolia* FISCH. are combined and used in the ratio of 1:0.1–5, preferably 1:1–2, on the basis of weight. Particularly, in the present invention it is preferable to extract the mixture of *Phellodendron amurense* RUPRECHT cortex and *Patrinia scabiosaefolia* FISCH. in the ratio of 1:1.

Hereinafter, the processes for producing both the mixed extracts according to the present invention are explained more in detail.

According to the process for producing the mixed aqueous extract of the present invention, in the first step, the dry mixture of *Phellodendron amurense* RUPRECHT cortex and *Patrinia scabiosaefolia* FISCH. is ground and extracted with water, for example, tap water or distilled water, under the saturated vapor pressure (121° C., 15 pound/in $a^2$) with heating. in the first step, water is used in the ratio of 10–45 parts by weight, preferably 25–35 parts by weight, with respect to one part by weight of plant materials.

Then, in the second step, the extracted solution is centrifuged to remove the precipitate and saturated again under high pressure, for example, by boiling, under vapor pressure (121° C., 15 pound/in $a^2$) in an autoclaving container to coagulate any remaining proteins. The coagulated protein is removed by filtration or centrifugation.

In the third step, the separated filtrate is used for organic solvent extract with an organic solvent such as chloroform, hexane, dichloromethane, cyclohexane, etc., preferably with chloroform or hexane to remove the impurities including resins, fibers, etc. Then, the aqueous layer is purified by using talc, etc. and lyophilized to obtain the desired mixed aqueous extract.

To prepare the mixed alcoholic extract of the present invention, in the first step, the dry mixture of *Phellodendron amurense* RUPRECHT cortex and *Patrinia scabiosaefolia* FISCH. is ground and extracted with an alcohol, preferably having 1 to 4 carbon atoms, for example, methanol, ethanol, etc.

In the first step, alcohol is used in the ratio of 5–40 pails by weight, preferably 10–20 parts by weight, with respect to one pail by weight of plant materials.

Then, in the second step the alcoholic extract is cooled and evaporated using rotatory evaporator to remove the alcohol. The residual alcoholic extract is solubilized by adding water and is boiled, and then, the resulting aqueous solution is filtered.

In this step, it is preferable that the amount of water is 5–30 times of mixed plant materials by weight, particularly 5–15 parts. After water is added to the alcoholic extract obtained by evaporating the mixture is boiled for a short time, generally for 5 to 10 minutes, to solubilize the alcoholic extract, and then filtered.

In the third step, from the separated filtrate organic solvent-soluble materials are extracted with an organic solvent such as chloroform, hexane, dichloromethane, cyclohexane, etc., preferably with chloroform or hexane to remove the impurities including resins, fibers, etc. Then, the aqueous layer is purified by using talc, etc. and lyophilized to obtain the desired mixed alcoholic extract.

As mentioned above, the mixed extract of *Phellodendron amurense* RUPRECHT cortex and *Patrinia scabiosaefolia* FISCH. exhibits a pharmacologically potent anti-HCV effect and an effect on the immune system related to T helper cells. Therefore, rendering it as an effective pharmaceutical composition for the treatment of hepatitis C.

In using the mixed extract of *Phellodendron amurense* RUPRECHT cortex and *Patrinia scabiosaefolia* FISCH. according to the present invention for the clinical purpose of treating hepatitis C, the mixed extract can be formulated alone or in the combination with a pharmaceutically acceptable carrier into a suitable pharmaceutical preparation according to the conventional method used in the pharmaceutical field, and then, administered according to a conventional manner used in the pharmaceutical field, preferably via oral route. In general, the composition of the present invention can be formulated into an oral administrating form, for example, tablets, capsules, solutions, powders, suspensions or syrups or can be prepared into a beverage.

The dose of the mixed extract of the present invention can vary depending on the following factors: the type of extract (aqueous or alcoholic), the severity of hepatitis, sex, age, body weight of the patient, and the kind of the desired effect, etc. The oral daily dose for an adult man is generally 5–50 mg, preferably 10–40 mg per 1 kg of body weight.

Further, if necessary, the mixed extract according to the present invention can be combined with, or administered together with, other agents such as agents for treating hepatitis, anti-inflammatory agents, anti-viral agents, etc. The agents which can be combined with, or administered together with, the composition according to the present invention comprise, for example, DDB (diphenyl dimethyl dicarboxylate), garlic oil, etc.

The present invention is more specifically explained by the following examples and experiments. However, it should be understood that the present invention is not limited to these examples in any manner.

EXAMPLE 1

Preparation of the mixed aqueous extract

The dry *Phellodendron amurense* RUPRECHT cortex and the dry *Patrinia scabiosaefolia* FISCH. were mixed in the ratio of 1:1 on the basis of weight and the mixture was ground using a mill. One hundred gram of the ground powdery mixture was taken and 3000 ml of distilled water was added thereto. The mixture was then boiled for 40–60 minutes under vapor pressure (121° C., 15 pound/in $a^2$) and the extracted solution was obtained after removing the water insoluble residue. The extracted solution was centrifuged and the precipitate was removed, and then the supernatant was concentrated with heating to reduce the total volume of the filtrate to 1500 ml and then filtered. The filtrate was saturated again for 15 minutes under vapor pressure (121° C. 15 pound/in $a^2$), centrifuged to remove the resulting precipitate including coagulated proteins and then filtered. The filtrate was introduced into a separatory funnel. 400 ml of chloroform was added thereto to extract resins and fibers and then the chloroform layer was separated and removed. The same procedure was repeatedly performed two times. Then, 200 ml of n-hexane was added to the aqueous layer to extract the remaining proteins, resins, fibers and n-hexane-soluble materials. The aqueous layer was separated, warmed to 60–80° C., stirred with 500 g of talc and then filtered under the reduced pressure to remove talc. The filtrate was slowly filtered again, and lyophilized. According to this method, about 15 g (yield: about 15% based on the dry weight) of the desired mixed aqueous extract was obtained from the mixture of *Phellodendron amurense* RUPRECHT cortex and *Patrinia scabiosaefolia* FISCH.

EXAMPLE 2

Preparation of the mixed alcoholic extract

The dry *Phellodendron amurense* RUPRECHT cortex and the dry *Patrinia scabiosaefolia* FISCH. were mixed in the ratio of 1:1 on the basis of weight and the mixture was ground using a mill. One hundred g of the ground powdery mixture was taken and 1500 ml of 70% ethanol was added thereto. The mixture was allowed to stand for 48–72 hours with stirring occasionally and then filtered under the reduced pressure to recover the alcoholic extract and to remove the residue. The alcohol was evaporated from the resulting alcoholic extract. The remaining alcoholic extract was mixed with 1000 ml of distilled water and boiled for 5 minutes. The resulting solution was subjected to the first purification by adding 500 g of talc thereto, stirring and filtering under the reduced pressure. The purified filtrate was introduced into a separatory funnel. Four hundred ml of chloroform was added thereto to extract resins and fibers and then the chloroform layer was separated and removed. The same procedure was repeatedly performed twice. Then, 200 ml of n-hexane was added to the aqueous layer to extract the remaining proteins, resins, fibers and n-hexane-soluble materials. The aqueous layer was separated, warmed to 60–80° C., stirred with 500 g of talc and then filtered under the reduced pressure to remove talc. The filtrate was slowly filtered again, and the filtrate was pulverized by lyophilization. According to this method, about 10 g (yield: about 10% based on dry weight) of the desired mixed aqueous extract was obtained from the mixture of *Phellodendron amurense* RUPRECHT cortex and *Patrinia scabiosaefolia* FISCH.

In the following examples for determining the characteristics of the extract of plant materials, all the extracts were obtained according to the same procedure as in Example 1.

EXAMPLE 3

Figure 2:
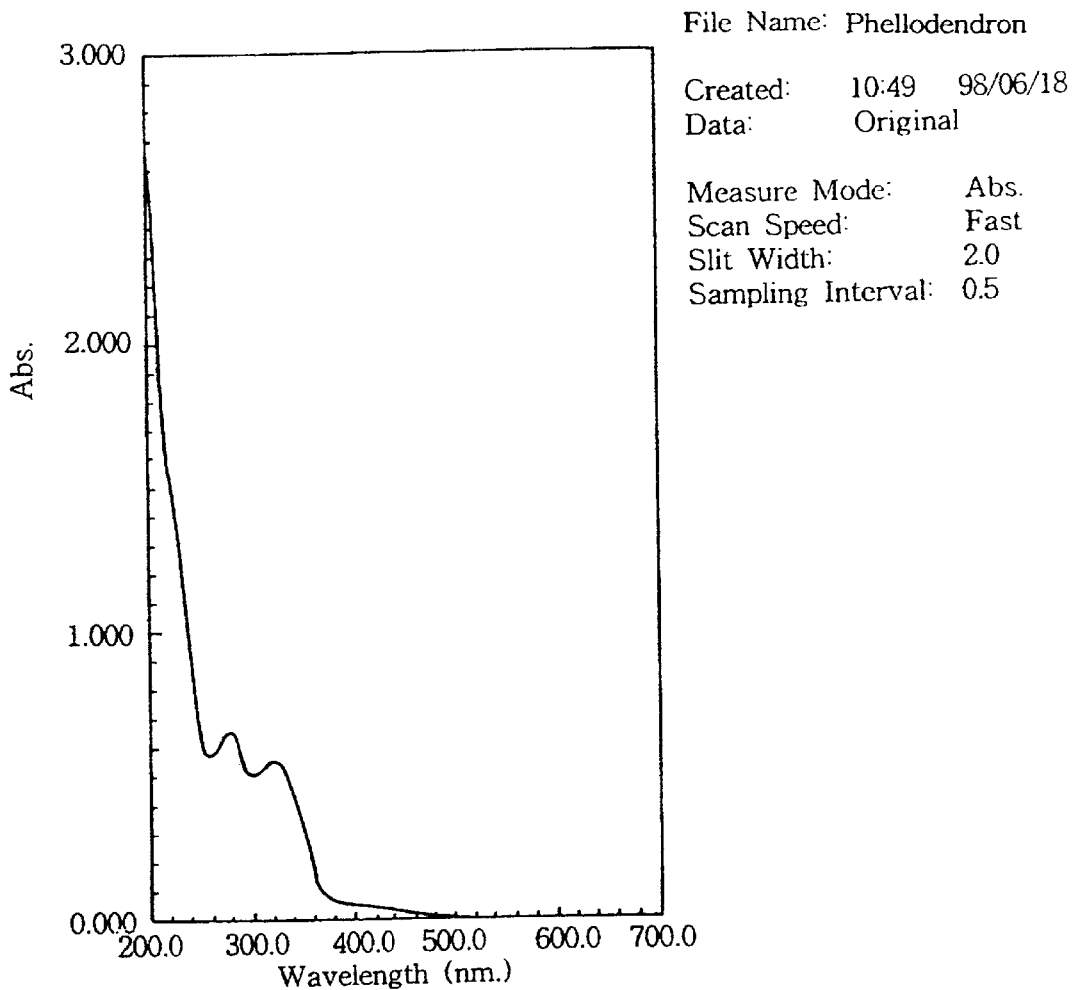
FIG. 2 represents UV scanning profile of an aqueous extract obtained from *Phellodendron amurense* RUPRECHT cortex.
Figure 3:
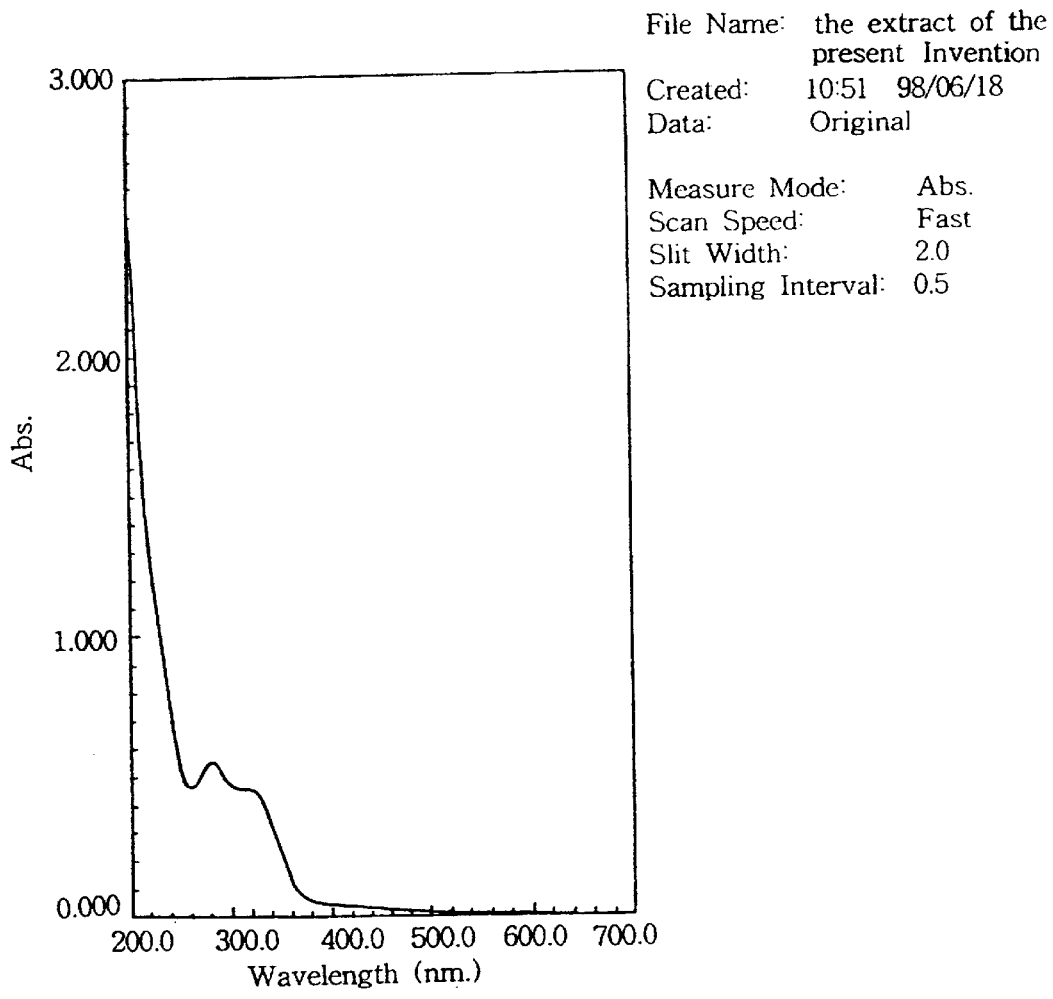
FIG. 3 represents UV scanning profile of a mixed aqueous extract of the present invention.

UV and HPLC characteristics of the mixed aqueous extract of the present invention The extracts of the present invention, namely *Patrinia scabiosaefolia* FISCH. and *Phellodendron amurense* RUPRECHT cortex and mixed plants were anolyzed by UV scanning (Shimazu, Japan) and HPLC ((Waters). FIG. 1 shows an UV scanning profile of the extract from Patrinia. FIG. 2 shows an UV scanning profile of the extract from Phellodendron. FIG. 3 shows an UV scanning profile of the mixed aqueous extract of the present invention.

Figure 4:
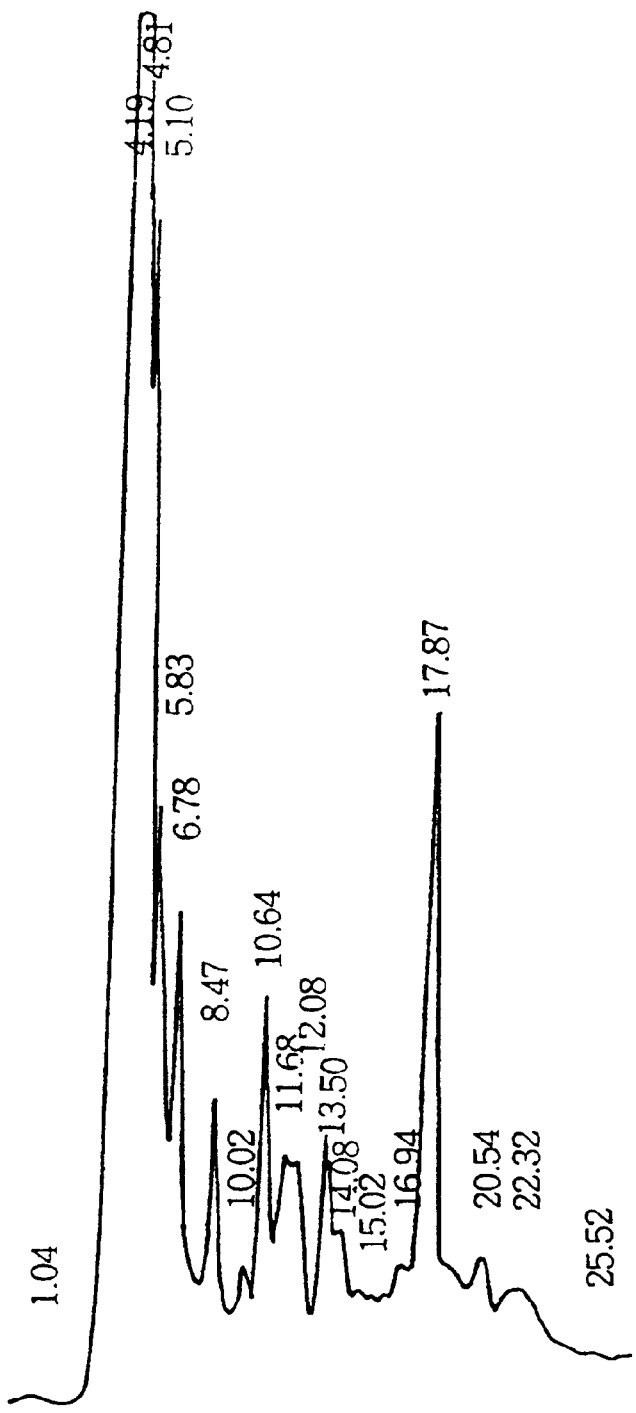
FIG. 4 represents HPLC profile of the aqueous extract obtained from *Patrinia scabiosaefolia* FISCH.
Figure 5:
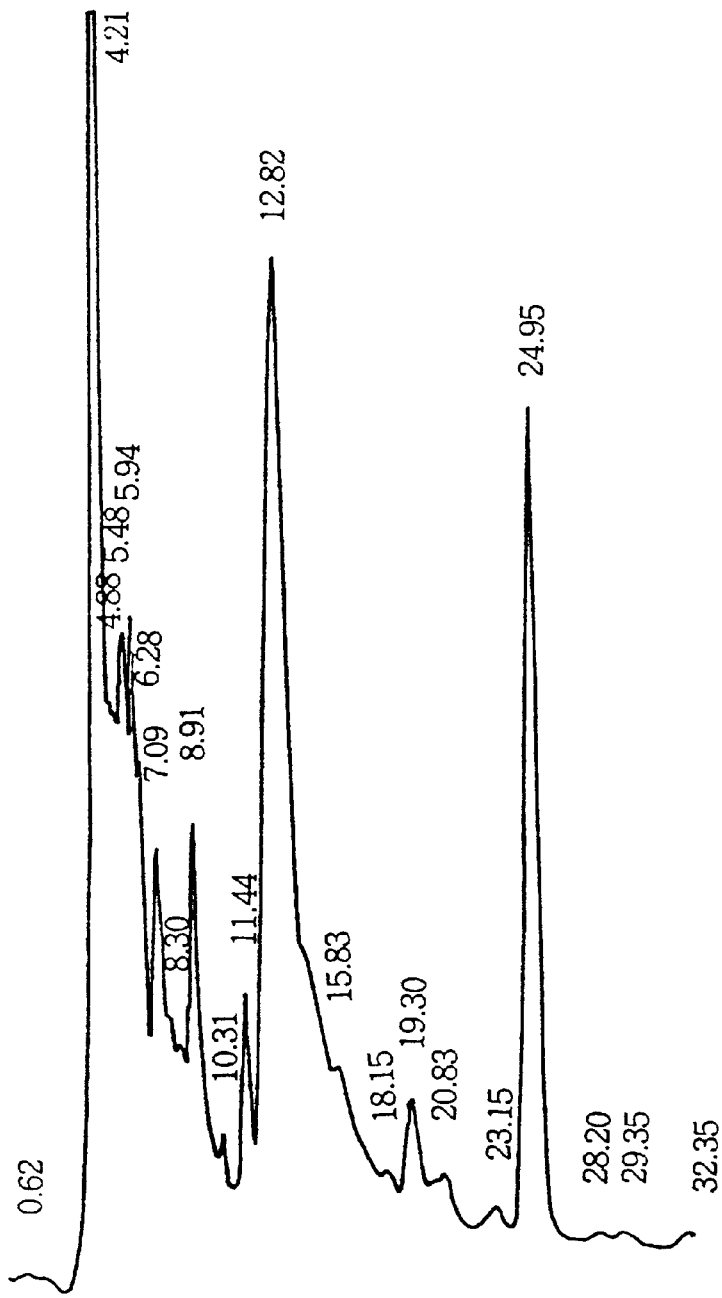
FIG. 5 represents HPLC profile of the aqueous extract obtained from *Phellodendron amurense* RUPRECHT cortex.
Figure 6:
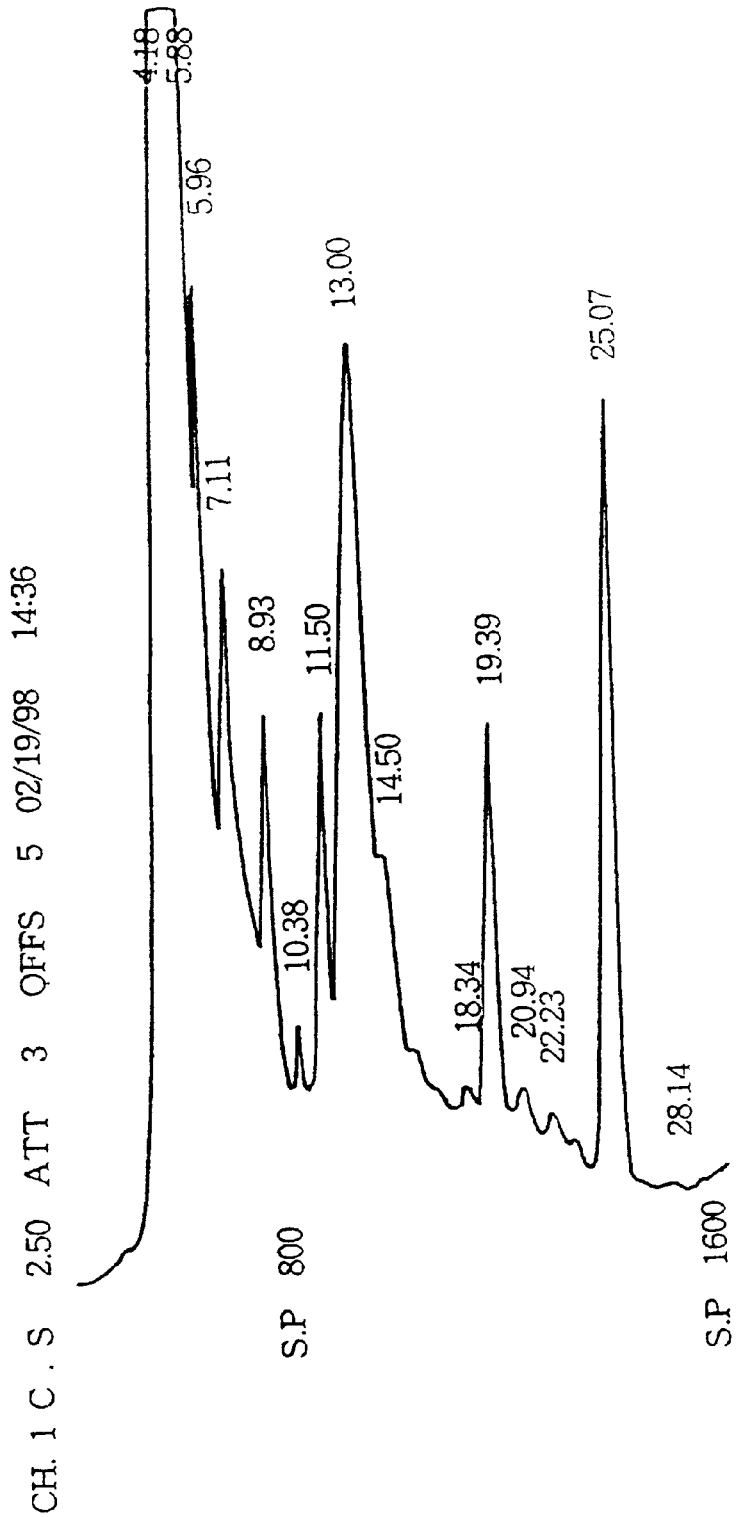
FIG. 6 represents HPLC profile of the mixed aqueous extract of the present invention.

For HPLC analysis, the extract from each plant and the extract of the present invention were dissolved in 50% methanol in the concentration of 1 mg/ml. Ten $\mu$L of the solution was injected into the HPLC (Waters 510). Inertsil ODS 3V (4.6 mm i.d.×250 mm L) reverse phase column was used, and mobile phase was 50% MeOH isocratic elution. Flow rate was 1.2 ml/min. Peaks were detected by UV detector at 254 nm. The characteristic peaks of each plant extract were observed in the HPLC profile. FIG. 4 shows a HPLC profile of the extract from *Patrinia scabiosaefolia* FISCH., and the characteristic peak of the extract from *Patrinia scabiosaefolia* FISCH. was revealed in the retention time of 18 min. FIG. 5 shows a HPLC profile of the extract from *Phellodendron amurense* RUPRECHT cortex, and the characteristic peak of the extract from *Phellodendron amurense* RUPRECHT cortex was revealed in 25 min. FIG. 6 shows a HPLC profile of the extract of the present invention, and the characteristic peaks were observed in 19 min. and 25 min. under the same HPLC condition as that for each plant. The characteristic peak in 19 min. is identified as a peak from the extract of *Patrinia scabiosaefolia* FISCH., and the characteristic peak in 25 min is identified as a peak from the extract of *Phellodendron amurense* RUPRECHT cortex. These two characteristic peaks in 19 min. and 25 min. were reproducible, and therefore they are considered as standard materials of each plant. The integrity of peak in 19 min. was 144.3±15.5 (Meant±S.E.: standard error), and peak height was 49.981±0.39. The Integrity of peak in 25 min. was 233.6±14.6, and peak height was 97.80±0.79.

From the results of UV scanning and HPLC analysis, we established the standardized method for the quality control of the extract of the present invention.

EXAMPLE 4

Analysis of elements of the mixed aqueous extract of the present invention

Elements of the mixed aqueous extract of the present invention were analysed by Elemental Analyzer (Carlo Erba/E.A. 1108). Table 1 shows that carbon, hydrogen, nitrogen and sulfur were contained in the mixed aqueous extract of the present invention.

TABLE 1

Elements of the extract of the present invention

| Elements | Percentage (%) |
|---|---|
| Carbon (C) | 44.1 |
| Hydrogen (H) | 5.9 |
| Nitrogen (N) | 0.5 |
| Sulfur (S) | 3 |
| Total | 53.5 |

EXAMPLE 5

Analysis of crude protein, fat and ash in the mixed aqueous extract of the present invention (1) Analysis of crude protein and nitrogen containing compound The content of nitrogen containing compound was investigated using the Kjeldahl Nitrogen Analysis Method. The method is briefly described below:

$$\text{Organic C, H, N} \xrightarrow[\text{Catalyst}]{H_2SO_4} CO_2 + H_2O + NH_4^+$$

Organic compounds containing nitrogen were degraded in the boiling $H_2SO_4$ to produce ammonium ion as a product. The amount of the resulting ammonium ion is quantified by titration with acid, and the content of nitrogen can be calculated.

The content of crude protein in the extract of the present invention was about 59.98% by Kjeldahl method.

(2) Analysis of crude fat

Crude fat in the extract of the present invention was extracted with ether. The ether was evaporated by rotatory evaporator, and dried extracted material was evaluated as a crude fat.

The content of the crude fat was about 2.29% by ether extraction.

(3) Analysis of crude ash

A sample of the extract of the present invention was burned at 500–500° C. An ash, representing the crude mineral fraction, remained unvolatilized. The content of the crude ash was about 9.68%.

EXAMPLE 6

Analysis of inorganic ions in the mixed aqueous extract of the present invention The composition of inorganic ions was investigated by ICP/AES (SHIMADZU ICPS-1000III) and ICP/MASS (Fisons PQ3 STEI). The results are described in the following Table 2.

| Operating Condition of ICP/AES (SHIMADZU ICPS-1000III) | |
|---|---|
| Forward power/W | 1200 |
| Cool gas flow/min. | 14 |
| Aux gas flow/min. | 0.4 |
| Neb gas flow/min. | 0.8 |
| Sample uptake rate/min. | 0.6 |
| Spray chamber: glass, water cooled, 0° C. | |
| Nebulizer: Meinhard concentric | |
| major elements (elements which are more than 100 ppm) | |

| Operating Condition of ICP/MASS (Fisons PQ3 STEI) | |
|---|---|
| Forward power/W | 1200 |
| Cool gas flow/min. | 14 |
| Aux gas flow/min. | 0.4 |
| Neb gas flow/min. | 0.8 |
| Sample uptake rate/min. | 0.6 |
| Spray chamber: glass, water cooled, 0° C. | |
| Nebulizer: Meinhard concentric | |

| Peak jumping acquisition parameters | |
|---|---|
| Point per peak: | 3 |
| Dwell time/ms: | 10.24 |
| Detector mode | PC |
| tract elements | (element which is less than 100 ppm) |

TABLE 2

Inorganic ions in the extract of the present invention and the extract of each plant

| | Phellodendron | Patrinia | Extract of the present invention | Unit |
|---|---|---|---|---|
| Mg | 0.51 | 0.53 | 0.43 | % |
| Ca | 1.56 | 1.05 | 1.27 | % |
| P | 0.20 | 0.21 | 0.25 | % |
| S | 0.16 | 0.21 | 0.24 | % |
| K | 1.93 | 1.95 | 2.78 | % |
| Na | 59 | 53 | 36 | ppm |
| Mn | 7 | 51 | 40 | ppm |
| Fe | 11 | 124 | 113 | ppm |
| Zn | 0.3 | 3 | 2 | ppm |
| Sr | 150 | 90 | 28 | ppm |
| Ba | 85 | 72 | 19 | ppm |
| Cr | 0.63 | 1.44 | 0.77 | ppm |
| Co | 0.19 | 0.31 | 0.58 | ppm |
| Ni | 1.74 | 2.51 | 2.25 | ppm |
| Cu | 2.57 | 7.23 | 0.95 | ppm |
| As | 0.27 | 1.05 | 1.06 | ppm |
| Cd | 0.01 | 0.03 | 0.02 | ppm |
| La | 0.07 | 0.06 | 0.09 | ppm |
| Pb | 0.11 | 1.07 | 0.32 | ppm |
| U | 0.11 | 0.25 | 0.53 | ppm |

Note:
Phellodendron = *Phellodendron amurense* RUPRECHT cortex
Patrinia = *Patrinia scabiosaefolia* FISCH.

As shown in Table 2, the amounts of heavy metal in the extract of the present invention were very low, and the extract of the present invention was thus proven harmless to the experimental animals and human.

EXAMPLE 7

Analysis of free sugars in the mixed aqueous extract of the present invention

The amount of flee sugars in the extract of the present invention was investigated by HPLC (Waters 510). Standard materials (Sigma) and the extract of the present invention were dissolved in the water ill the concentration of 10 mg/ml and filtered by syringe filter (0.45 μm). Twenty μl of each sample was injected into the HPLC.

HPLC condition
 column: Aminex HPX (300×7.8 mm) with Micro-guard Carbo-P (Bio-Rad Laboratories)

Detector: R401 Waters (Attenuation 32)
Oven Temperature: 80° C.
Mobile phase: $H_2O$
Flow rate: 0.6 ml/min.

Figure 7:
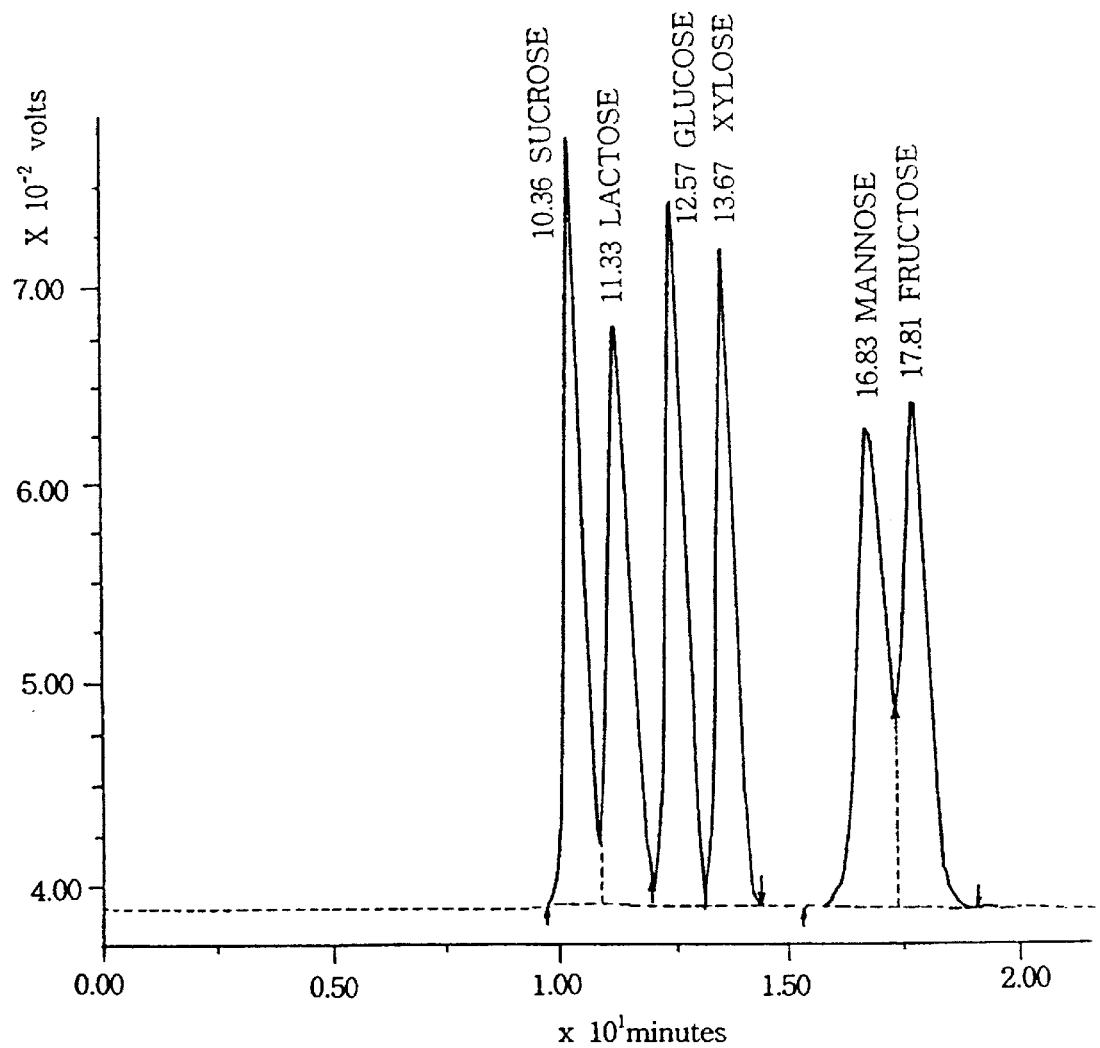
FIG. 7 represents HPLC profile of standard sugars, namely sucrose, lactose, glucose, xylose, mannose and fructose.
Figure 8:
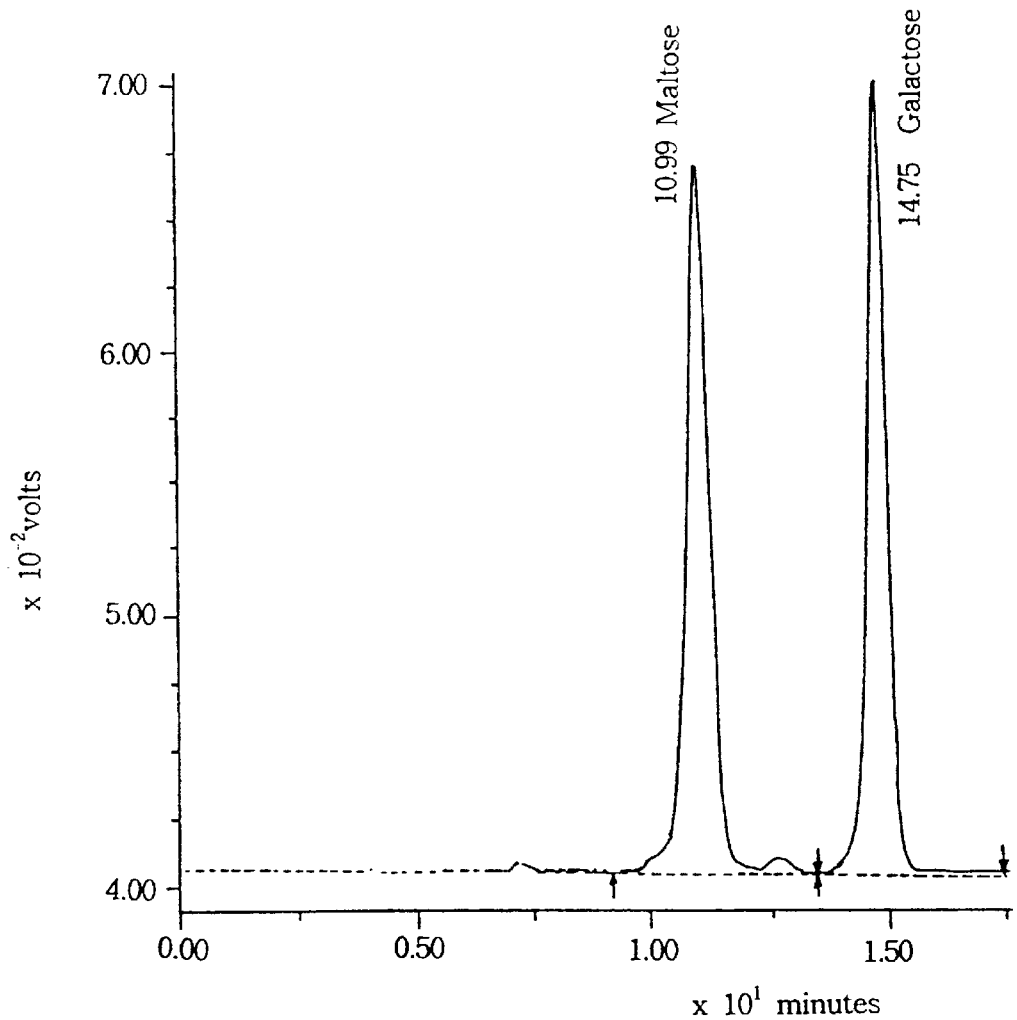
FIG. 8 represents HPLC profile of standard sugars, namely maltose and galactose.
Figure 9:
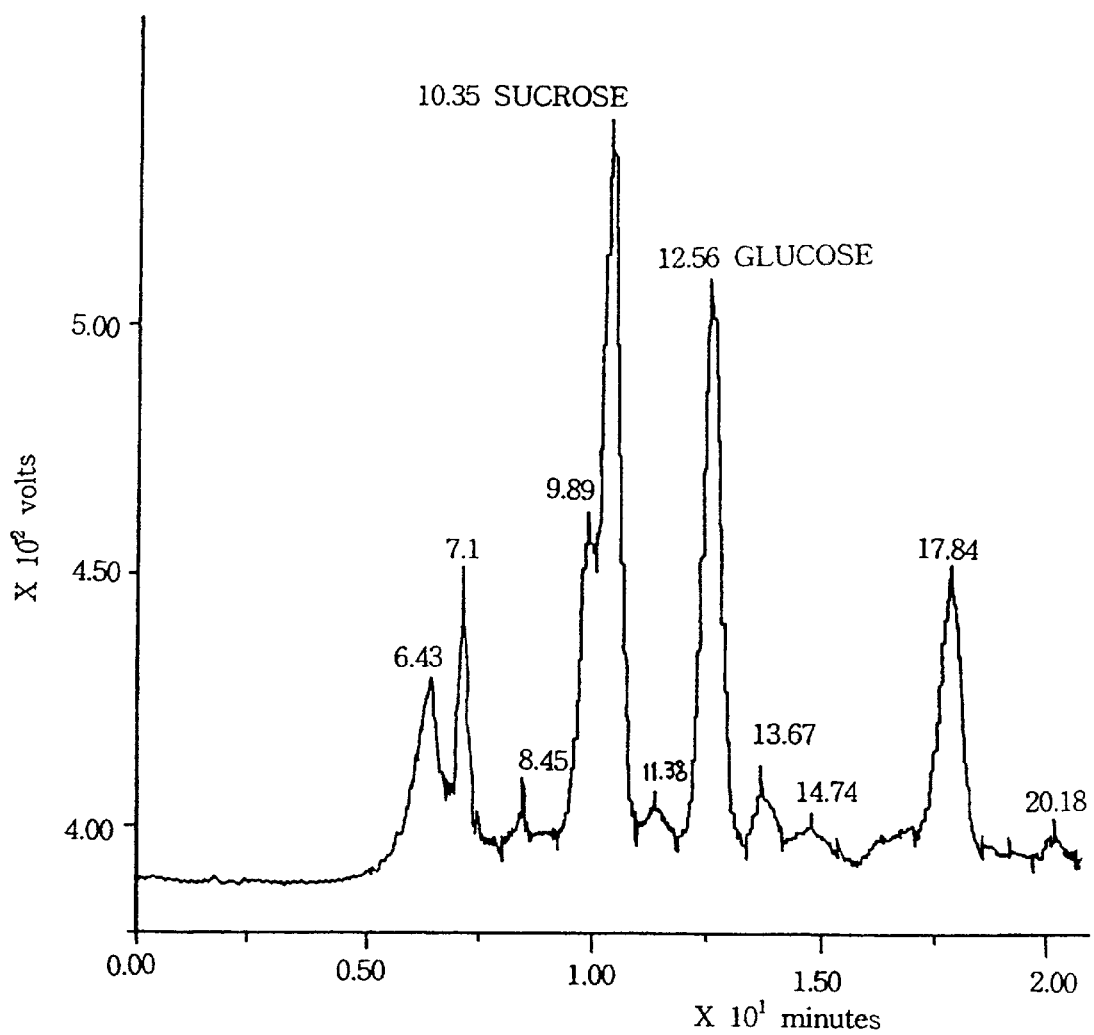
FIG. 9 represents HPLC profile of the sugars in the mixed aqueous extract of the present invention.

FIGS. 7 and 8 show HPLC chromatogram of the standard sugars, namely sucrose, lactose, glucose, xylose, mannose, fructose, maltose and galactose. FIG. 9 shows HPLC chromatogram of the extract of the present invention. The amount of sugars in the mixed aqueous extract of the present invention was calculated as mg/g extract (Table 3).

TABLE 3

Amount of sugars in the mixed aqueous extract of the present invention

| sugar | standard area | sample area | quantity (mg/g) |
|---|---|---|---|
| sucrose | 1,012,701 | 386,803 | 95.49 |
| lactose | 965,878 | 15,952 | 4.13 |
| glucose | 997,443 | 311,634 | 78.11 |
| xylose | 931,997 | 26,295 | 7.05 |
| fructose | 942,416 | 181,245 | 48.08 |
| galactose | 904,934 | 9,355 | 2.58 |
| total | | | 235.45 |

EXAMPLE 8

Analysis of amino acids in the mixed aqueous extract of the present invention

Amino acids composition of the extract of the present invention and the extract of each plant (*Patrinia scabiosaefolia* FISCH. and *Phellodendron amurense* RUPRECHT cortex) was analyzed using HPLC (Pharmacia). One hundred /ig of each sample was hydrolyzed with 6N HCl using Pico-tag method. Free amino acids were labeled with PITC (phenyl isothiocyanate). The sample was injected into HPLC with reverse phase ODS column, and the peaks were detected by UV detector at 254 nm.

Figure 10:
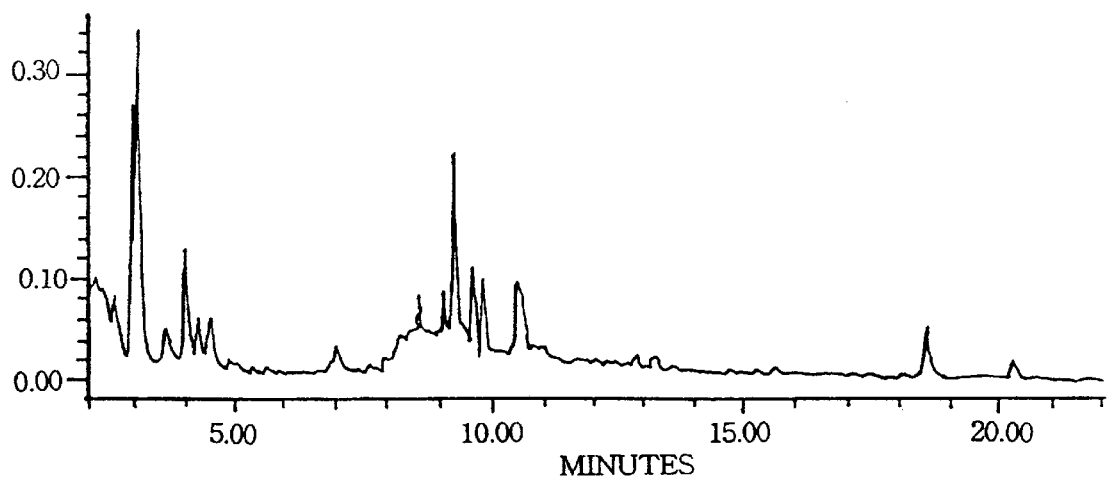
FIG. 10 represents amino acid analysis chromatogram of the aqueous extract obtained from *Patrinia scabiosaefolia* FISCH.
Figure 11:
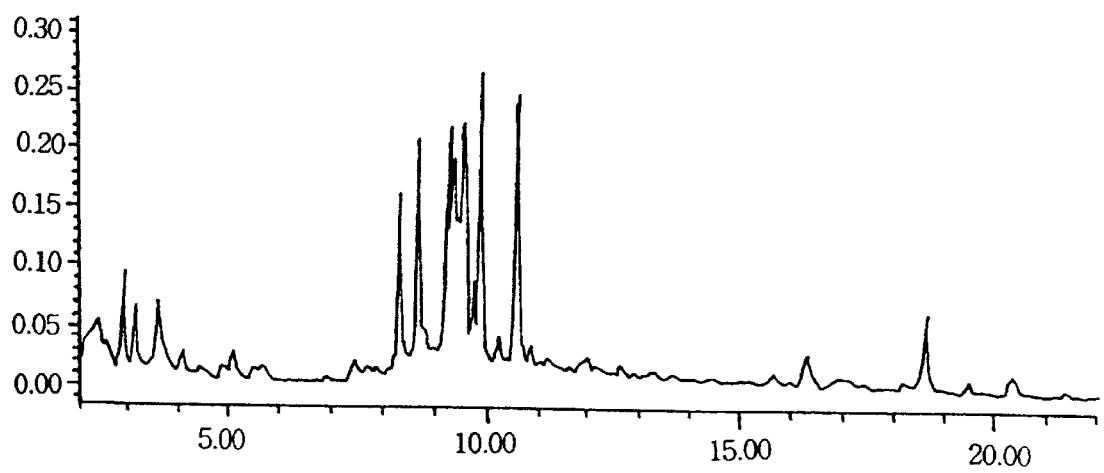
FIG. 11 represents amino acid analysis chromatogram of the aqueous extract obtained from *Phellodendron amurense* RUPRECHT cortex.
Figure 12:
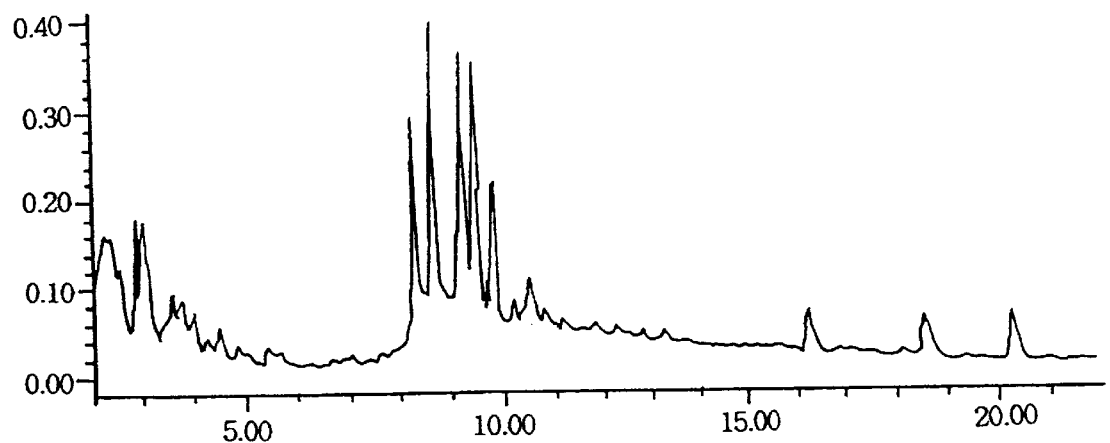
FIG. 12 represents amino acid analysis chromatogram of the mixed aqueous extract of the present invention.

FIG. 10 shows amino acid analysis chromatogram of the extract of *Patrinia scabiosaefolia* FISCH., and FIG. 11 shows amino acid analysis chromatogram of the extract of *Phellodendron amurense* RUPRECHT cortex. FIG. 12 shows amino acid analysis chromatogram of the mixed aqueous extract of the present invention.

As shown in Table 4, the amount of polar amino acids containing acidic and basic amino acids was high in the extract of the present invention.

TABLE 4

Amount of amino acids in the extract of *Patrinia scabiosaefolia* FISCH., or *Phellodendron amurense* RUPRECHT cortex, and the mixed aqueous extract of the present invention.

| | Phellodendron | Patrinia | Extract of the present invention | Retention time |
|---|---|---|---|---|
| Asp | 1492.7 | 1030.2 | 1198.1 | 3.6 |
| Glu | 417.7 | 1878.1 | 1436.8 | 4.0 |
| Ser | 333.1 | 65.0 | 196.3 | 7.6 |
| Gly | 1494.2 | 445.1 | 3621.1 | 8.3 |
| His | 1827.9 | 273.4 | 622.6 | 8.8 |
| Arg | 1664.6 | 621.1 | 4829.5 | 9.1 |
| Thr | 2418.3 | 1969.9 | 3430.3 | 9.3 |
| Ala | 645.5 | 917.2 | 955.3 | 9.7 |
| Pro | 1775.3 | 622.3 | 1749.3 | 9.8 |
| Tyr | 123.5 | 28.9 | 894.4 | 12.2 |
| Val | 239.9 | 141.2 | 931.6 | 12.9 |
| Met | 248.6 | 67.7 | 689.6 | 13.7 |
| Cys2 | 96.5 | 43.1 | 362.3 | 14.7 |
| Ile | 69.4 | 48.9 | 202.1 | 15.3 |
| Leu | 236.2 | 78.6 | 467.9 | 15.6 |
| Phe | 65.9 | 35.6 | 145.1 | 17.4 |
| Trp | 183.1 | 36.8 | 367.3 | 18.1 |
| Lys | 79.5 | 10.7 | 23.9 | 19.5 |

Note:
Phellodendron = *Phellodendron amurense* RUPRECHT cortex
Patrinia = *Patrinia scabiosaefolia* FISCH.

EXAMPLE 9

Analysis of alkaloids and organic acids in the mixed aqueous extract of the present invention The extracts of each of *Patrinia scabiosaefolia* FISCH and *Phellodendron amurense* RUPRECHT cortex and the mixture thereof according to the present invention were fractionated by solvent extraction using dichloro-methane, ethyl acetate, n-butanol and water in accordance with a method depicted in the following scheme:

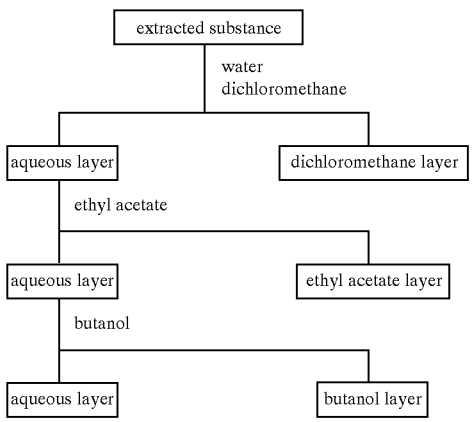

In the above depicted method, each solvent was used in a sufficient amount for the extraction and tile use of next solvent was decided by TLC.

Each fraction was separated by column chromatography again.

For the separation of dichloromethane phase, the silica gel column was used. The mobile phase for the silica gel column (3 cm×130 cm) was the gradient system of dichloromethane and methanol (flow rate 1.5 ml/min.). Sephadex LH20 column (3 cm×130 cm) was used for the ethyl acetate and butanol phase, and the gradient system of water and methanol was used for the mobile phase (flow rate 1.5 ml/min.).

Large scale of each fraction from the column chromatography was prepared by preparative HPLC (Pharmacia) again. For the preparative HPLC, reverse phase column was used, and the mixture of methanol and water was used for the mobile phase. Flow rate was 4.0 ml/min. Peaks were detected by UV detector at 254 nm. The structure of single compounds which were isolated from preparative HPLC was elucidated by $^1H$ NMR ($^1H$ nuclear magnetic resonance spectroscopy: AQMS-500/Bruker) and MASS (HP5988A Quadropole Mass Spectrometer). $^1H$ NMR spectrum was compared with standard materials (Sigma Chemical Co., St. Louis. Mo., U.S.A.).

The composition of the extract of the present invention is shown in Table 5.

TABLE 5

Composition of the mixed aqueous extract of the present invention

| Components | Content (%) |
|---|---|
| Crude Protein and Nitrogen Containing Compound | 59 |
| Crude Fat | 2 |
| Crude Ash | 9 |
| Sugars | 23 |
| Alkaloids: | |
| Berberine, Palmatine | 4 |
| Organic acid: | |
| benzoic acid glycoside | |
| ferulic acid glycoside | 3 |
| caffeic acid glycoside | |
| 3,4-dihydroxy benzoic acid | |

Administration forms

The administration form of the anti-HCV agents of the present invention is not particularly restricted and can be appropriately selected according to requirements. The examples of the administration forms include peroral agents such as tablet, capsule, granule, powder and liquid preparation.

Herein after, the examples of the administration forms containing the mixed aqueous extract of *Phellodendron amurense* RUPRECHT cortex and *Patrinia scabiosaefolia* FISCH. according to the present invention are specifically illustrated. In addition, it should be understood that the mixed alcoholic extract can also be formulated according to the same manner.

Administration form Example 1: Tablets

In order to prepare 250 mg tablets of the lyophilized powdery mixed aqueous extract of *Phellodendron amurense* RUPRECHT cortex and *Patrinia scabiosaefolia* FISCH. as obtained in Example 1 was blended with 260 mg of lactose as the diluent and 35 mg of avicel (microcrystalline cellulose) as the excipients, 15 mg of sodium starch glyconate as the disintegrants, and 80 mg of L-HPC (low-hydroxypropylcellulose) as the binder. The blend was introduced into a U-type mixer and then mixed for about 20 minutes. After the mixing was completed, 10 mg of magnesium stearate as the lubricant was further added thereto and then mixed for about 3 minutes. The mixture was compressed into tablets according to a conventional manner and then subjected to film-coating to prepare the tablet containing 250 mg of the mixed aqueous extract.

Administration form Example 2: Syrups

A suitable amount of white sugar was dissolved in a given amount of water, and 80 mg of paraoxymethylbenzoate and 16 mg of paraoxypropylbenzoate as the preservatives were added thereto. The lyophilized powdery mixed aqueous extract of the present invention(4.5 g) as obtained in Example 1 was added thereto and completely dissolved at 60° C. The resulting solution was cooled and distilled water was added thereto to adjust the total volume to 150 ml. According to this procedure, the syrup containing 30 mg of the mixed aqueous extract per 1 ml was prepared.

Administration form Example 3: Capsules

Three hundred mg of the lyophilized powdery mixed aqueous extract of *Phellodendron amurense* RUPRECHT cortex and *Patrinia scabiosaefolia* FISCH. as obtained in Example 1 was mixed with 200 mg of lactose as the carrier. The mixture was filled in hard gelatine capsules to prepare the capsule preparation containing 300 mg of the mixed aqueous extract.

Administration form Example 4 Beverage Preparation

Five hundred mg of the lyophilized powdery mixed aqueous extract of *Phellodendron amurense* RUPRECHT cortex and *Patrinia scabiosaefolia* FISCH. as obtained in Example 1 was dissolved in the suitable amount of water and then suitable amounts of vitamin C as the auxiliary component and citric acid. Sodium citrate and high fructose as the agent for correcting taste were added thereto. Then, a suitable amount of sodium benzoate as the preservative was added and then water was added thereto to adjust the total volume to 100 ml. According to this method, the desired beverage composition was prepared.

Experiment 1

Effects of the mixed aqueous extract on elimination of hepatitis C virus in human trial The clinical trial was conducted by administering the mixed aqueous extract of *Phellodendron amurense* RUPRECHT cortex and *Patrinia scabiosaefolia* FISCH. according to the present invention to six patients suffering from hepatitis C.

Figure 13A:
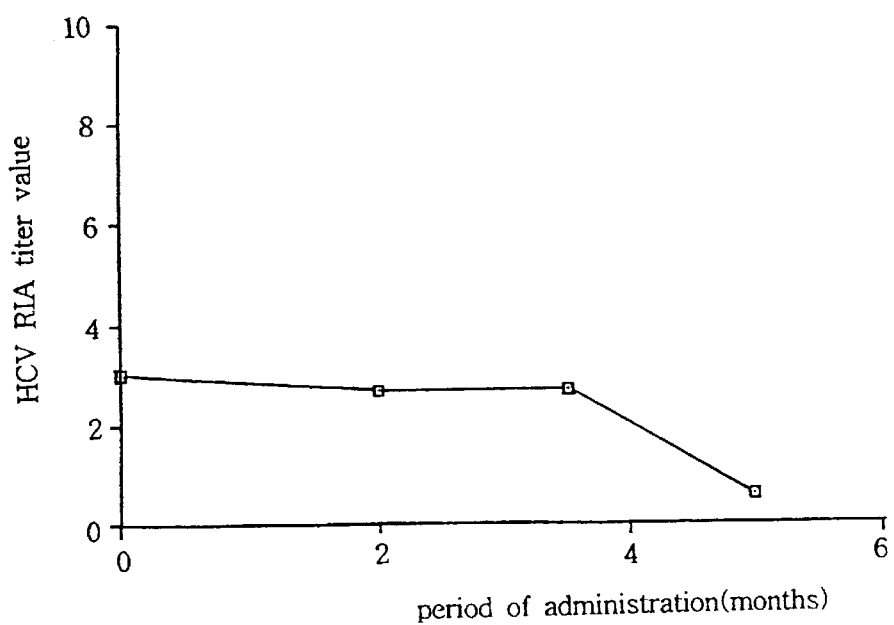
[FIG. 13A: case 1.
Figure 13B:
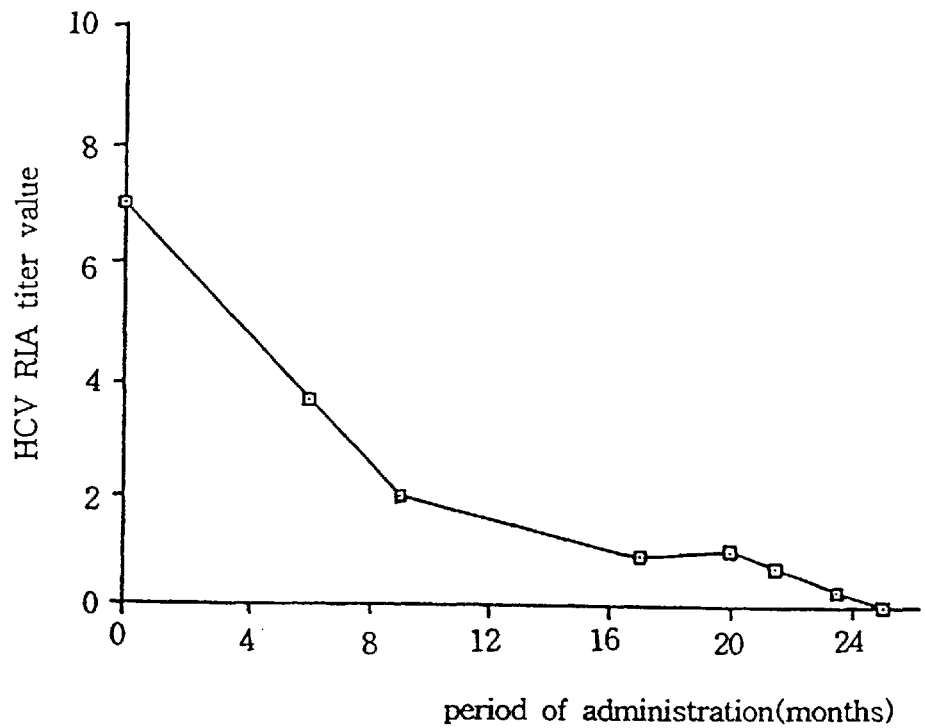
FIG. 13B: case 2.
Figure 13C:
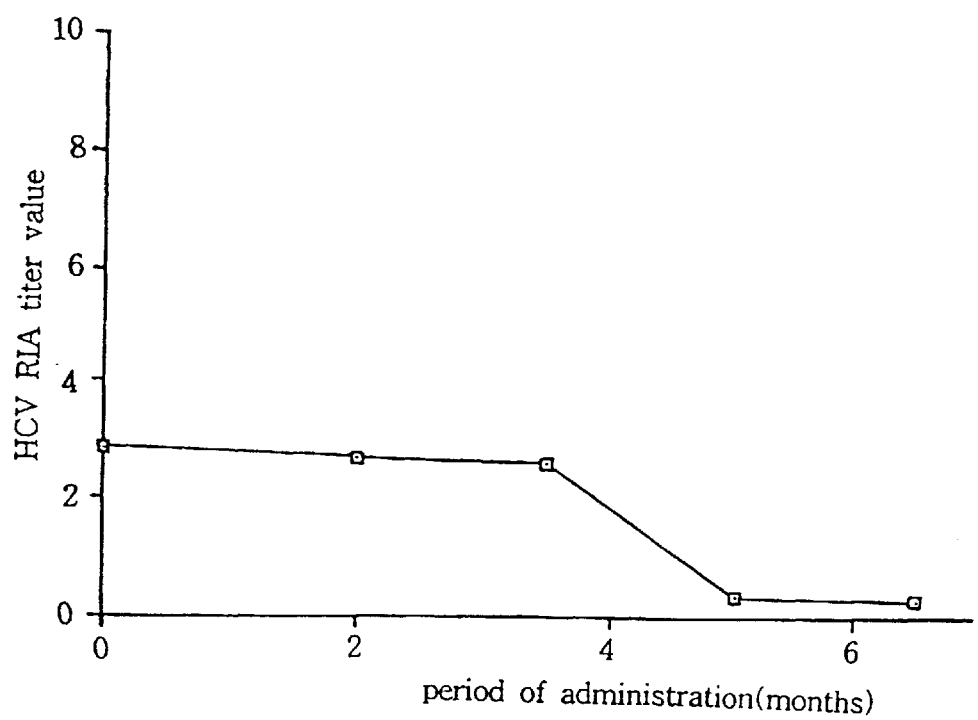
FIG. 13C: case 3, FIG. 13D case 4.
Figure 13D:
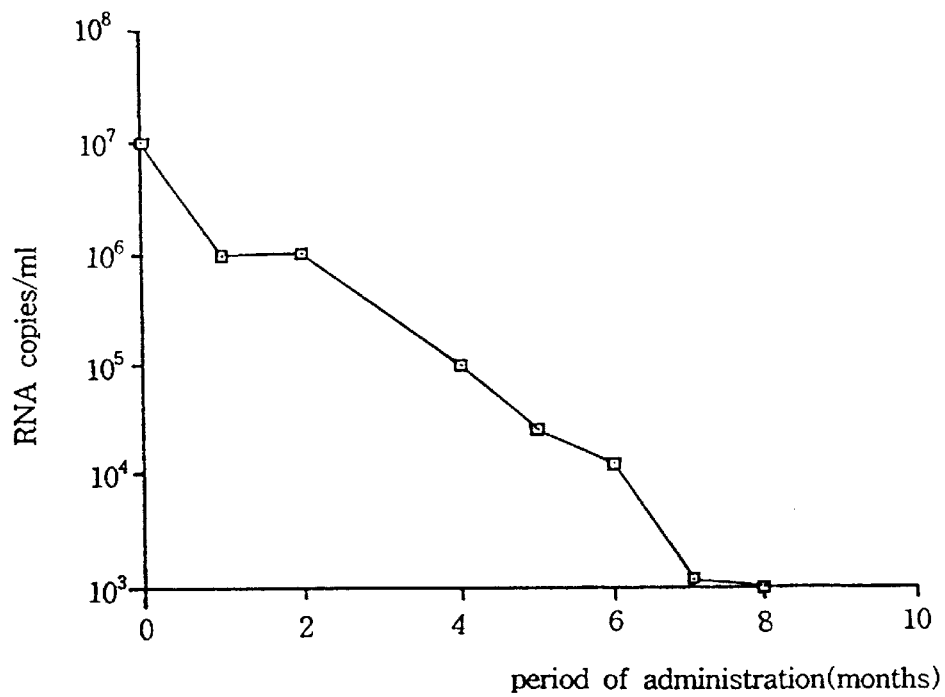
FIG. 13 is a graph showing the results of clinical trials. According to Experiment 1, the mixed aqueous extract of the present invention was orally administered to patients suffering from hepatitis C. Anti-viral effects were expressed by antibody titer or mRNA copy numbers
FIG. 13E: case 5, FIG. 13F case 6]
Figure 13E:
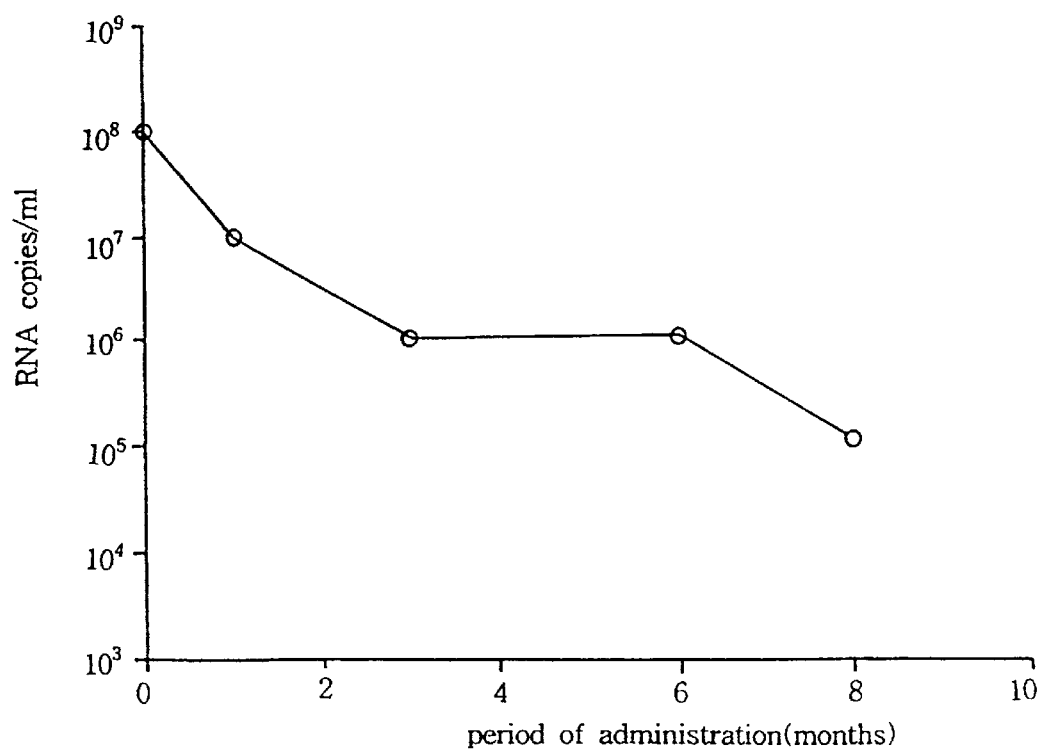
Figure 13F:
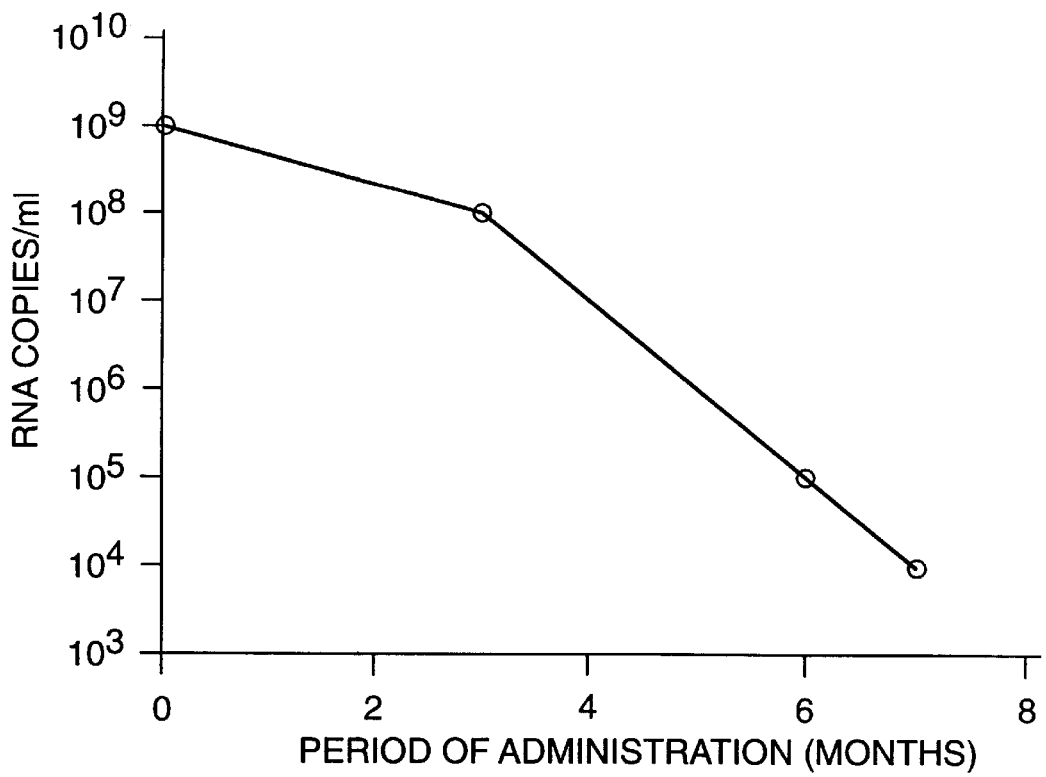

The results were expressed as antibody titer values obtained from examining anti-HCV antibody by RIA (radioimmuno assay) in cases 1 to 3, and as RNA copy numbers of HCV measured by means of RT-PCR in cases 4 to 6. In case 1 (FIG. 13A) for a patient diagnosed with chronic hepatitis C, it can be identified that the administration of the mixed aqueous extract of the present invention for 5 months in an amount of 2000 mg per day resulted in a decrease of the antibody titer value nearly to 0. In case 2, for a 7-years old patient suffering from chronic hepatitis C, the antibody titer value was as high as 7 before treatment and decreased nearly to 0 after 24 months by continuous administration of the mixed aqueous extract of the present invention in an amount of 2000 mg per day. Case 3 is for a patient suffering from chronic hepatitis B and C. As can be seen from FIG. 13C, it was observed that the administration of the mixed aqueous extract of the present invention for 5 months in an amount of 2000 mg per day resulted in a decrease of the antibody titer value for HCV nearly to 0. In case 4 (FIG. 13D), for a patient suffering from chronic hepatitis C, RNA copy number per 1 ml of patient's serum as measured by RT-PCR method was $1\times10^7$ before treatment, and decreased to $1\times10^6$ after one month administration of the mixed aqueous extract of the present invention in an amount of 2000 mg per day and was not detected after 6 months treatment since it was reduced under $1\times10^3$ as the cut-off value. For cases 5 and 6, the mixed aqueous extract was administered in an amount of 2000 mg per day and HCV was measured using RT-PCR method. In case 5 (FIG. 13E), for a patient suffering from hepatitis C who had HCV for 15 years, the number of virus in 1 ml of patient's serum decreased from $1\times10^8$ to $1\times10^5$ after 8 months treatment. In case 6 (FIG. 13F), for a patient suffering from hepatitis C who had HCV for 20 years, HCV RNA copy number decreased from $1\times10^9$ to $1\times10^4$ per 1 ml of serum, after administration of the mixed aqueous extract of the present invention for 7 months.

From the results of clinical trial as mentioned above, it can be concluded that the mixed aqueous extract of the present invention is very effective for the treatment of hepatitis C.

Experiment 2

Figure 14:
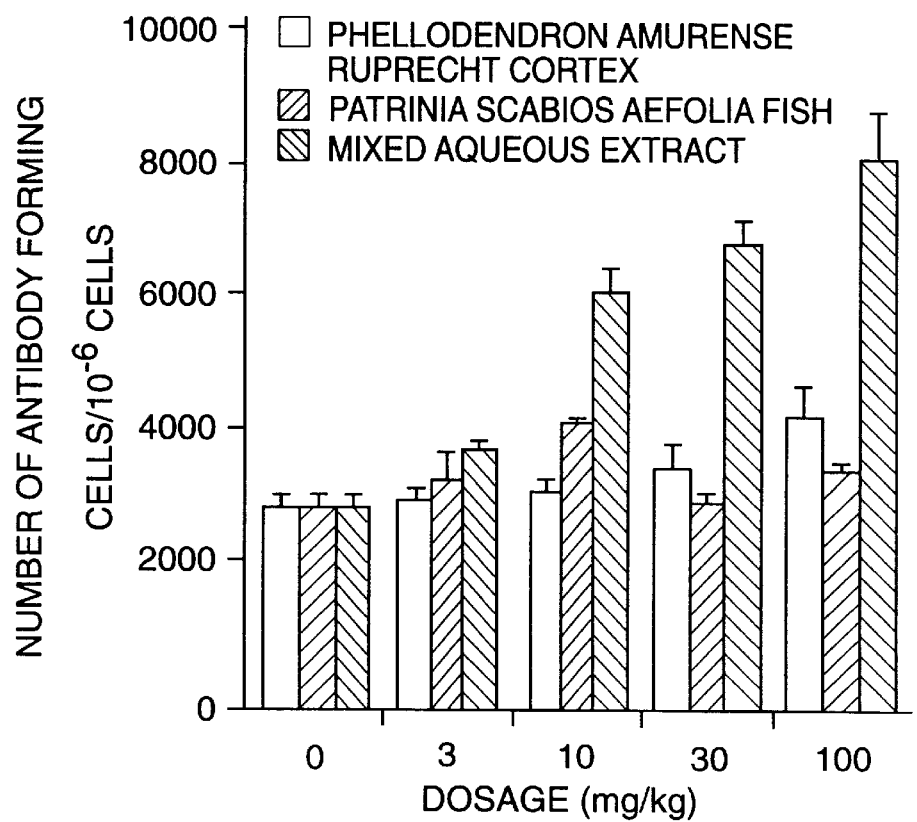
FIG. 14 is a graph showing the effects of aqueous extracts from each *Phellodendron amurense* RUPRECHT cortex and *Patrinia scabiosaefolia* FISCH. or the mixture thereof on T cell-dependent antibody forming reaction in vivo.

Effects of the mixed aqueous extract on T cell-dependent antibody forming reaction in vivo Balb/c mice (n=65) weighing 17–20 g were divided into 13 groups of 5 mice. $2.4\times10^8$ SRBC (Sheep Red Blood Cells) were intraperitoneally transplanted to the test animal in each group. Each of the mixed aqueous extract of the present invention obtained in Example 1, and the aqueous extracts of each medicinal plants, *Phellodendron amurense* RUPRECHT cortex and *Patrinia scabiosaefolia* FISCH. was administered via oral route in an amount of 3, 10, 30, 100 mg per day, for 3 days (0, 1, 2 day) from the first day of transplantation. The control group received only physiological saline via oral route. After 4 days, each test animal was sacrificed and spleen was aseptically removed, minced and then passed through a mesh to separate spleen cells, and isolated by a syringe plunger in petri dish containing 3 ml of EBSS (Earle's Balanced Salt Solution). The resulting cell suspension was transferred to a 15 ml conical tube and allowed to stand for 5 minutes. Then, 2 ml of the supernatant was taken and centrifuged at 1200 rpm for 10 minutes. The supernatant was discarded and the residue was suspended again in 2 ml of EBSS and diluted 30 times with EBSS. The resulting spleen cell dilution was used for a plaque-forming cell analysis in an amount of 100 µl each time. One hundred µl of the spleen cell dilution as obtained above was mixed with SRBC (25 µl, target cell) washed with EBSS, guinea pig complement (25 µl) diluted two times with EBSS and agarose (0.85% in EBSS, 350 µl), solidified in a petri dish and then maintained in a $CO_2$ incubator at 37° C. (for about one hour. Then, the plaques and cells were counted according to a modified Jerne Plaque Assay [see, Hwan M. Kim, et al., J. Toxicological Sciences 21:41–45, 1996], and the results were expressed as the number of antibody forming cells per $1 \times 10^6$ cells. The average values of the results are shown in the following Table 6 and FIG. 14.

TABLE 6

Effects of the aqueous extracts from each single plants or the mixed plants of the present invention on T cell-dependent antibody forming reaction in vivo

| Test groups | Antibody forming cells (per $10^6$ cells) | | |
| --- | --- | --- | --- |
| | Aqueous extract of PA | Aqueous extract of PS | Mixed aqueous extract |
| Control group | 2672 ± 135 | 2672 ± 135 | 2672 ± 135 |
| 3 mg/kg dosage group | 2845 ± 245 | 3212 ± 454 | 3690 ± 98 |
| 10 mg/kg dosage group | 2996 ± 273 | 4036 ± 46 | 6072 ± 444 |
| 30 mg/kg dosage group | 3391 ± 484 | 2920 ± 105 | 6844 ± 456 |
| 100 mg/kg dosage group | 4208 ± 548 | 3408 ± 72 | 8215 ± 533 |

Note:
1) PA: *Phellodendron amurense* RUPRECHT cortex
2) PS: *Patrinia scabiosaefolia* FISCH.
3) Mixed aqueous extract: Aqueous extract of the mixture of *Phellodendron amurense* RUPRECHT cortex and *Patrinia scabiosaefolia* FISCH. obtained in Example 1

As can be seen from the above results, the mixed aqueous extract according to the present invention increases the antibody forming cells in proportion to the administration doses of the extract and thus, the 100 mg/kg dosage group shows an increase in the number of antibody forming cells by 307% in comparison to the control group. In addition, even in comparison to the group in the treatment of the extract from each single plant with an amount of 100 mg/kg, the number of antibody forming cells increased far better in the group to which the mixed aqueous extract of two medicinal plants was administered in an amount of 10 mg/kg, which is only one-tenths of the dosage of the extract of each medicinal plant. From this result, it can be seen that the mixed aqueous extract of the present invention exhibits a synergistic effect which is far superior to the effect of the extract of each medicinal plant. Therefore, it can be concluded that the mixed aqueous extract of *Phellodendron amurense* RUPRECHT cortex and *Patrinia scabiosaefolia* FISCH. exhibits a superior synergistic reinforcing effect on the immune system.

In addition, the reinforcing effect on the immune system of the mixed aqueous extract prepared in Example 1 was compared with that of the mixed alcoholic extract prepared in Example 2. Specifically, the test was conducted using each of the mixed aqueous extract and the mixed alcoholic extract in an amount of 100 mg/kg, according to the same method as above to measure the number of antibody forming cells. The obtained results are shown in the following Table 7 and FIG. 15.

TABLE 7

Effects of the mixed aqueous extract and the mixed alcoholic extract of the present invention on T cell-dependent anti-body forming reaction in vivo

| Test groups | Number of antibody forming cells (DPM/250,000 cells) |
| --- | --- |
| Control group | 3219 ± 104 |
| Mixed aqueous extract 100 mg/kg dosage group | 8021 ± 360 |
| Mixed alcoholic extract 100 mg/kg dosage group | 12021 ± 1254 |

Figure 15:
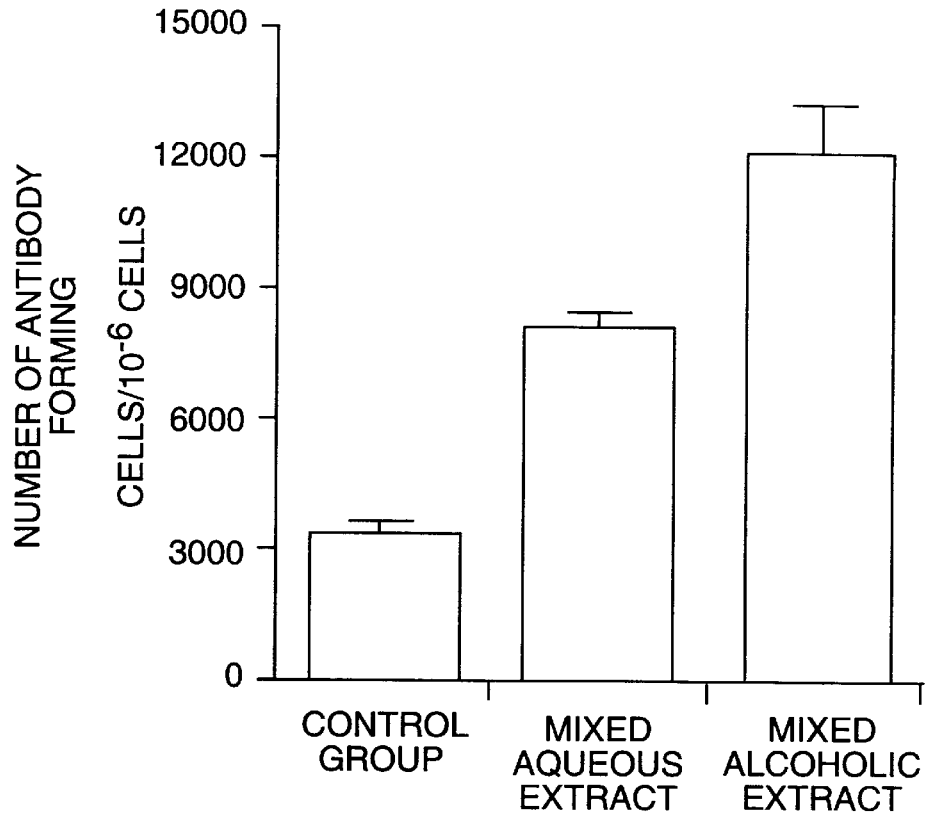
FIG. 15 is a graph showing the effects of the mixed aqueous extract and the mixed alcoholic extract of *Phellodendron amurense* RUPRECHT cortex and *Patrinia scabiosaefolia* FISCH. according to the present invention on T cell-dependent antibody forming reaction in vivo.

From the results shown in the above Table 7 and FIG. 15, it is shown that both the mixed aqueous extract and the mixed alcoholic extract of the present invention increase the number of antibody forming cells and, particularly, the mixed alcoholic extract increases more effectively the number of antibody forming cells by 51% in comparison to the mixed aqueous extract.

Experiment 3

Effects of the mixed aqueous extract on T cell activation

The effects of the mixed aqueous extract of *Phellodendron amurense* RUPRECHT cortex and *Patrinia scabiosaefolia* FISCH. according to the present invention on T cell activation was determined by the mixed immunocyte reaction method.

Spleen was aseptically removed from two kinds of mice having different MHC (major histocompatibility complex) antigen, i.e. B6C3F1 (H-2k) and BDF1 (H-2d) mice, minced and then passed through a mesh to separate the spleen cells. The separated spleen cells were adjusted to $2.5 \times 10^6$ cells/ml media (EBSS). Then, each of B6C3F1 (H-2k) and BDF1 (H-2d) spleen cells was added to a 96-well plate in an amount of 100 µl per well, and the final volume of each well was brought to 200 µl of EBSS.

The spleen cells were treated with the mixed aqueous extract prepared by Example 1 in the concentration of 0.01 to 100 µg/ml, and then incubated in a $CO_2$ incubator at 37° C. for 3 days. One µCi of [$^3$H]-thymidine was added to each well and incubated for another 18 hours. Cells were collected by means of an automatic cell harvester and then the absorbance of [H]-thymidine was measured with Beta Counter (Beckman LSC) to determine the proliferation of immunocyte. The obtained results are shown in the following Table 8 and FIG. 16.

TABLE 8

Effects of the mixed aqueous extract of the present invention on the proliferation of T cells

| Test conditions | Degree of proliferation (DPM/250,000 cells) |
| --- | --- |
| Control group with saline treatment | 3809 ± 419 |
| Mixed aqueous extract 0.01 μg/ml treated group | 4329 ± 522 |
| Mixed aqueous extract 0.03 μg/ml treated group | 5245 ± 611 |
| Mixed aqueous extract 0.1 μg/ml treated group | 6769 ± 916 |
| Mixed aqueous extract 0.3 μg/ml treated group | 7146 ± 410 |
| Mixed aqueous extract 1 μg/ml treated group | 9008 ± 1046 |
| Mixed aqueous extract 3 μg/ml treated group | 10243 ± 1034 |
| Mixed aqueous extract 10 μg/ml treated group | 10792 ± 611 |
| Mixed aqueous extract 30 μg/ml treated group | 11178 ± 1332 |
| Mixed aqueous extract 100 μg/ml treated group | 11045 ± 1364 |

Figure 16:
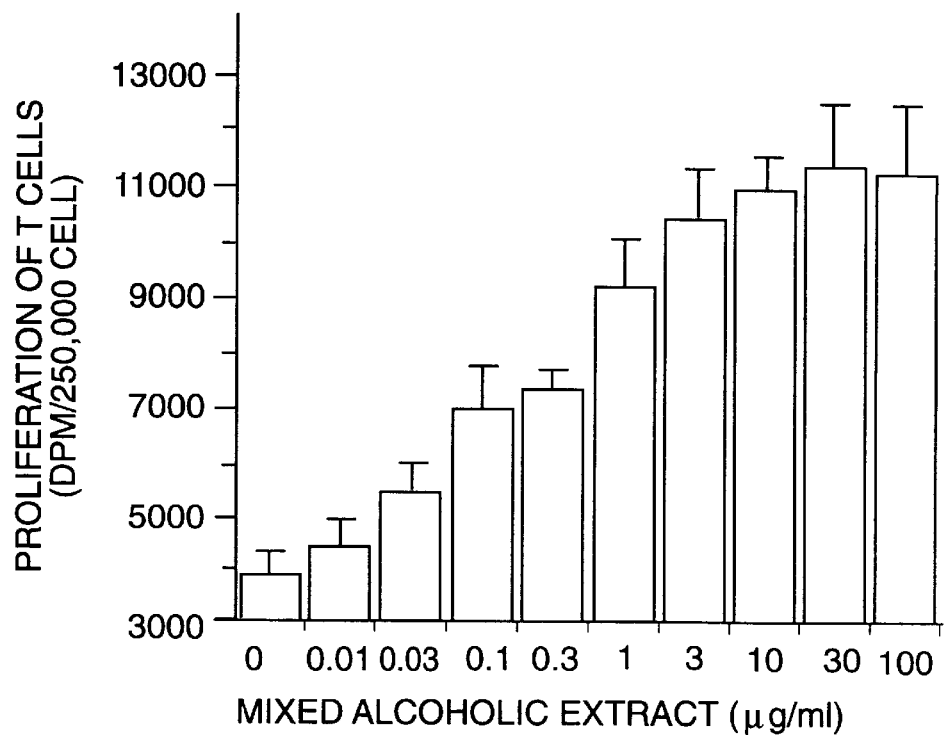
FIG. 16 is a graph showing the effects of the mixed aqueous extract of *Phellodendron amurense* RUPRECHT cortex and *Patrinia scabiosaefolia* FISCH. according to the present invention on proliferation of T cells.

From the results shown in the above Table 8 and FIG. 16, it is demonstrated that the mixed aqueous extract of the present invention increases the proliferation of T cells in proportion to its concentration as used.

Experiment 4

Effects of the mixed aqueous extract on the proliferation of immunocyte

Mice were sacrificed by cervical dislocation, then the spleen was removed and washed with buffer solution (EBSS). Spleen cells were isolated by means of a plunger of syringe. The suspension containing spleen cells thus obtained was transferred to a tube and allowed to stand for about 5–10 minutes. The supernatant was collected and centrifuged (1200 rpm, 10 minutes). The supernatant was discarded and the precipitate was resuspended in RPMI1640 culture medium [10% FCS (fetal calf serum), 2-mercaptoethanol (2-ME)] to measure the cell number and to determine the survival rate of cells. The separated spleen cells were adjusted to the concentration of $10^6$ cells/ml media, dispensed in a 96-well plate in an amount of 200 μl per well, treated with the mixed aqueous extract prepared by Example 1 according to the present invention in the concentration of 0.01 to 100 μg/m), and then incubated for 3 days on a rocking plate in an incubator under 5 psi of mixed gas (7% $O_2$, 10% $CO_2$, 83% $N_2$). After incubation, [$^3$H]-thymidine was added to the plate in the concentration of 5 μCi/ml and then the absorbance was measured with Beta Counter to determine the degree of the proliferation of splenocytes. The results are shown in the following Table 9 and FIG. 17.

TABLE 9

Effects of the mixed aqueous extract of the present invention on the proliferation of splenocytes

| Test conditions | Degree of proliferation (DPM/200,000 cells) |
| --- | --- |
| Control group with saline treatment | 748 ± 104 |
| Mixed aqueous extract 0.01 μg/ml treated group | 737 ± 72 |
| Mixed aqueous extract 0.03 μg/ml treated group | 768 ± 123 |
| Mixed aqueous extract 0.1 μg/ml treated group | 727 ± 91 |
| Mixed aqueous extract 0.3 μg/ml treated group | 922 ± 25 |
| Mixed aqueous extract 1 μg/ml treated group | 1115 ± 142 |
| Mixed aqueous extract 3 μg/ml treated group | 1585 ± 169 |
| Mixed aqueous extract 10 μg/ml treated group | 2903 ± 225 |
| Mixed aqueous extract 30 μg/ml treated group | 4587 ± 396 |
| Mixed aqueous extract 100 μg/ml treated group | 5587 ± 265 |

Figure 17:
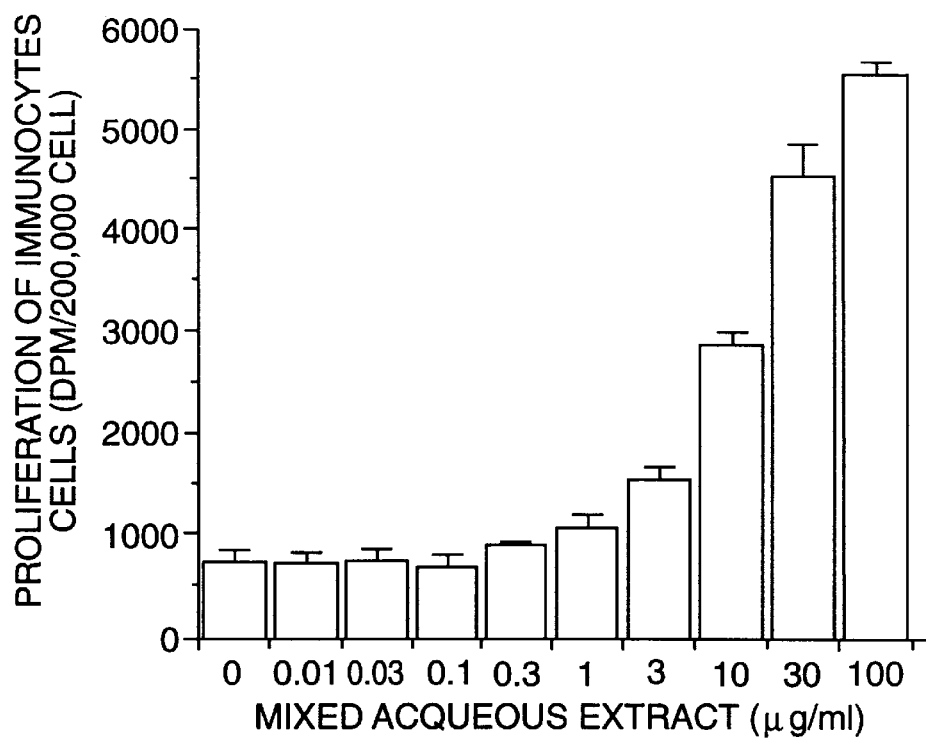
FIG. 17 is a graph showing the effects of the mixed aqueous extract of *Phellodendron amurense* RUPRECHT cortex and *Patrinia scabiosaefolia* FISCH. according to the present invention on proliferation of immunocytes.

From the results shown in the above Table 9 and FIG. 17, it may be implied that the mixed aqueous extract of the present invention increases the proliferation of immunocytes in proportion to its concentration as used.

Experiment 5

Effects of the mixed aqueous extract in combination with lectin phytoaglutinine on the proliferation of T-helper cells In order to more clearly examine the effects of the mixed aqueous extract of the present invention on the proliferation of T helper cells, the mixed aqueous extract of the present invention was combined with phytoaglutinine (PHA), which is one of the standard mitogens stimulating the proliferation of the CD4 T-cells. Specifically, according to the same method as in Experiment 2, spleen cells aseptically separated from mouse were adjusted to the concentration of $0.5 \times 10^7$ cells/ml and then dispensed in a 96-well plate in an amount of 200 μl per well. Four μl of PHA at the concentration of 250 μg/ml was added to wells to make the final concentration of 5 μg/ml. The plate was then treated with the mixed aqueous extract prepared by Example 1 according to the present invention in the concentration of 0.01 to 100 μg/ml, and then incubated for 3 days in a $CO_2$ incubator at 37° C. T-cell proliferation was evaluated by measuring the [$^3$H] thymidine uptake of T-cells according to the same method as Experiment 3. The control group was not treated with the mixed aqueous extract of the present invention. The obtained results are shown in the following Table 10 and FIG. 18.

TABLE 10

Effects of the mixed aqueous extract of the present invention in combination with lectin on the proliferation of immunocytes

| Test conditions | Degree of proliferation (DPM/200,000 cells) |
| --- | --- |
| Control group with saline treatment | 616 ± 60 |
| Mixed aqueous extract 0.01 μg/ml treated group | 637 ± 78 |
| Mixed aqueous extract 0.03 μg/ml treated group | 703 ± 92 |
| Mixed aqueous extract 0.1 μg/ml treated group | 715 ± 88 |
| Mixed aqueous extract 0.3 μg/ml treated group | 799 ± 79 |
| Mixed aqueous extract 1 μg/ml treated group | 907 ± 103 |
| Mixed aqueous extract 3 μg/ml treated group | 986 ± 65 |
| Mixed aqueous extract 10 μg/ml treated group | 1281 ± 72 |
| Mixed aqueous extract 30 μg/ml treated group | 2210 ± 102 |
| Mixed aqueous extract 100 μg/ml treated group | 2806 ± 95 |

Figure 18:
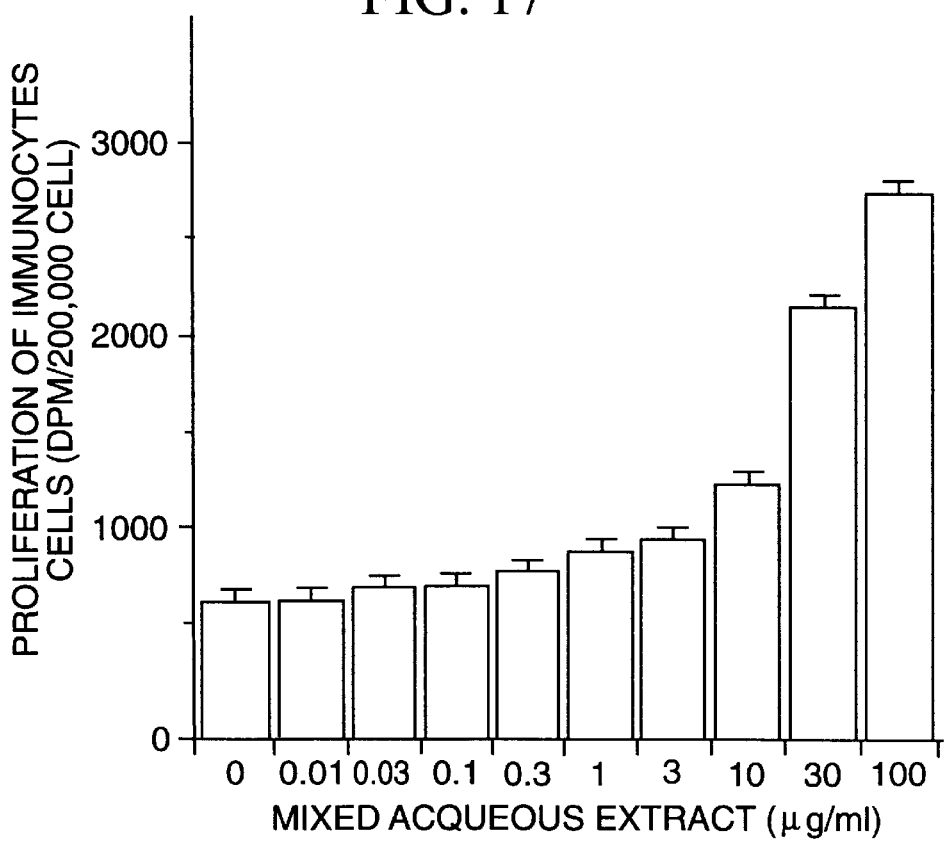
FIG. 18 is a graph showing the effects of the mixed aqueous extract of *Phellodendron amurense* RUPRECHT cortex and *Patrinia scabiosaefolia* FISCH. according to the present invention on the proliferation of immunocytes induced by immunocytes mitogen, lectin (PHA)

From the results shown in the above Table 10 and FIG. 18, it may be suggested that the mixed aqueous extract of the present invention combined with PHA remarkably increases the proliferation of immunocytes in proportion to its concentration as used.

Experiment 6

Changes in the distribution ratio of immunocytes in spleen, thymus and bone marrow due to in vivo treatment with the mixed aqueous extract The mixed aqueous extract of *Phellodendron amurense* RUPRECHT cortex and *Patrinia scabiosaefolia* FISCH. as prepared by Example 1 according to the present invention was orally administered to mice in the concentration of 100 and 300 mg/kg for 3 days, and then mice were sacrificed to remove spleen, thymus and bone marrow. The immunocytes were separated from these removed organs according to the same manner as the method in Experiment 2, and then centrifuged. The supernatant was discarded, and the cell precipitate was treated for 2 to 3 minutes with erythrocytolysis buffer solution (ACK buffer, 0.15M $NH_4Cl$, 0.01M $KHCO_3$, 0.1 mM $Na_2EDTA$, pH 7.2) in an amount of 1 ml per organ. The immunocytes were washed with medium, adjusted to the concentration of $10^7$ cells/ml, and then dispensed into tubes in an amount of 100 μl per tube. To determine B cells rat monoclonal antibody B220 for mouse B cells combined to phycoerythrin was used; for T cells Thy-1-PE (Caltag Laboratories) was used; for CD4 T cells CD4-FITC (Caltag Laboratories) was used; and for CD8 T cells Ly2-FITC (Caltag Laboratories) was used. These antibodies were added to tubes respectively, and then allowed to react for 40 minutes over ice. After completion of the reaction, the tube was washed with phosphate buffered saline (PBS) and then subjected to measurement of the constitutional ratio of each immunocyte by means of FACScan (Becton Dickenson, San Jose, Calif.). The obtained results are shown in the following Table 11.

TABLE 11

Changes in the constitutional ratio of immunocytes with the mixed aqueous extract of the present invention (unit: %)

| Organs | Dosage | B cell | T cell | CD4 T cell | CD8 T cell |
|---|---|---|---|---|---|
| Spleen | Control group | 37.09 | 25.73 | 22.93 | 10.35 |
| | MAE 100 mg/kg | 43.25 | 36.22 | 29.03 | 13.95 |
| | MAE 300 mg/kg | 44.35 | 37.30 | 28.65 | 9.90 |
| Thymus | Control group | | 88.48 | 72.43 | 74.71 |
| | MAE 100 mg/kg | | 86.13 | 78.64 | 71.49 |
| | MAE 300 mg/kg | | 94.12 | 76.34 | 73.00 |
| Bone marrow | Control group | 65.53 | | | |
| | MAE 100 mg/kg | 87.62 | | | |
| | MAE 300 mg/kg | 85.35 | | | |

Note:
MAE = Mixed aqueous extract of *Phellodendron amurense* RUPRECHT cortex and *Patrinia scabiosaefolia* FISCH. according to the present invention.

According to the result obtained by examining 10,000 cells, as described in the above Table 11, the constitutional ratios of B cells, T cells and CD4 T cells in spleen were increased; and in thymus the distribution ratio of T cells was increased and the ratio of CD4 T cells was also increased. In bone marrow, the constitutional ratio of B cells was increased. From this result, it is demonstrated that the mixed extract of *Phellodendron amurense* RUPRECHT cortex and *Patrinia scabiosaefolia* FISCH. according to the present invention reinforces the immune system, particularly T helper cells to increase the resistance against hepatitis C virus.

Experiment 7
Anti-oxidant activity of the mixed aqueous extract of the present invention It is known that substances having anti-oxidant activity, also has anti-viral activity including hepatitis C. Anti-oxidant activity of the mixed aqueous extract of the present invention was determined by using a chemiluminescence assay. An ABEI-microperoxidase-$H_2O_2$ system was used to assay the anti-oxidant activity of the extract of the present invention. Microperoxidase, aminobutylethylisoluminol (ABEI), and $H_2O_2$ were purchased from Sigma chemical company, St. Louis, Mo., U.S.A.

ABEI was used at the concentration of 0.18 μM. Extracts being assayed were used at 10 mg/ml as a maximum concentration and also at 10 times serial dilutions. Two hundred μl of ABEI and 200 ml of extracts were put in polystyrene tube suitable for use in a Berthold 9502 luminometer. Hydrogen peroxide (0.35%) and microperoxidase (0.01 mg/ml) were autoinjected into the tube to start the oxidative reaction. The luminescence was measured for 2 seconds using a Berthold Luminometer 9502. Distilled water was used for control.

In general, an anti-oxidant prevents the oxidative reaction, resulting in the decrease of the light intensity in this assay system. Thus, the anti-oxidant activity can be evaluated by the degree of decrease in the light intensity. According to FIG. 20, the extract of the present invention shows the excellent anti-oxidant activity. Those results represent that the extract of the present invention contains potent anti-oxidants. The extract of the present invention has higher anti-oxidant activity than the extract of each plant and therefore, it is concluded that the mixed aqueous extract of the present invention has a synergistic anti-oxidant effect of each plant extract.

Experiment 8
Toxicity test

To evaluate the safety of the mixed aqueous extract of *Phellodendron amurense* RUPRECHT cortex and *Patrinia scabiosaefolia* FISCH., the $LD_{50}$ value of the mixed extract, as the standard index for acute toxicity, was determined according to the following method.

Thirty normal ICR mice (♀, 19±1 g) were used as the experimental animal and divided into 5 groups wherein each group contains 6 mice. The mixed aqueous extract of *Phellodendron amurense* RUPRECHT cortex and *Patrinia scabiosaefolia* FISCH. prepared in Example 1 according to the present invention was orally administered to Group A in an amount of 3 g and, with gradually increasing the amount, to Group B in an amount of 6 g, to Group C in an amount of 9 g, to Group D in an amount of 12 g and to Group E in an amount of 15 g. Then, the $LD_{50}$ value of the mixed aqueous extract administered via oral route was determined on the 7th day after oral administration of the mixed aqueous extract by Behrens-Kärber method. The result is described in the following Table 12.

TABLE 12

Lethal dose ($LD_{50}$) of the mixed aqueous extract of the present invention administered via oral route

| Test group | Dosage (g/kg) | Oral administration (p.o.) Number of animals died/ Number of experimental animals | *Z | **d |
|---|---|---|---|---|
| A | 3 | 0/6 | — | — |
| B | 6 | 0/6 | 0 | 3 |
| C | 9 | 0/6 | 0 | 3 |
| D | 12 | 0/6 | 0 | 3 |
| E | 15 | 0/6 | 0 | 3 |

Note:
*z: Half value (½) of the number of animals died at two consecutive dosages
**d: Difference between two consecutive dosages From the result described in the above Table 12, since no animal died even in the group to which the mixed aqueous extract of *Phellodendron amurense* RUPRECHT cortex and *Patrinia scabiosaefolia* FISCH. according to the present invention is administered, in a high dosage of 15 g per 1 kg of body weight, it is concluded that the oral $LD_{50}$ value of the mixed aqueous extract is more than 15 g/kg and, therefore, the mixed aqueous extract of the present invention is very safe. In other words, it is apparently noted that the mixed aqueous extract of *Phellodendron amurense* RUPRECHT cortex and *Patrinia scabiosaefolia* FISCH. according to the present invention can be safely administered without any toxicity.

The autopsy and pathohistological assay for the experimental animals used for the measurement of $LD_{50}$ value were conducted according to the following manner. On the one week after oral administration, all the viable animals were anesthetized with ether and the blood was collected from the vein. Then, the desired organs were removed and any abnormality of the organs was macroscopically examined. To conduct the pathohistological assay, all the dissected organs were fixed in 10% neutral formalin solution for 10 days or more, and then dried, embedded with a paraffin embedder (Fisher, Histomatic Tissue Processor, 166A, Shadon, UK), cut off in 5 μm section by means of AO Rotary Microtome (LEICA, Germany) and then stained with hematoxylin and eosin. The condition of stained organs was microscopically observed.

Figure 19A:
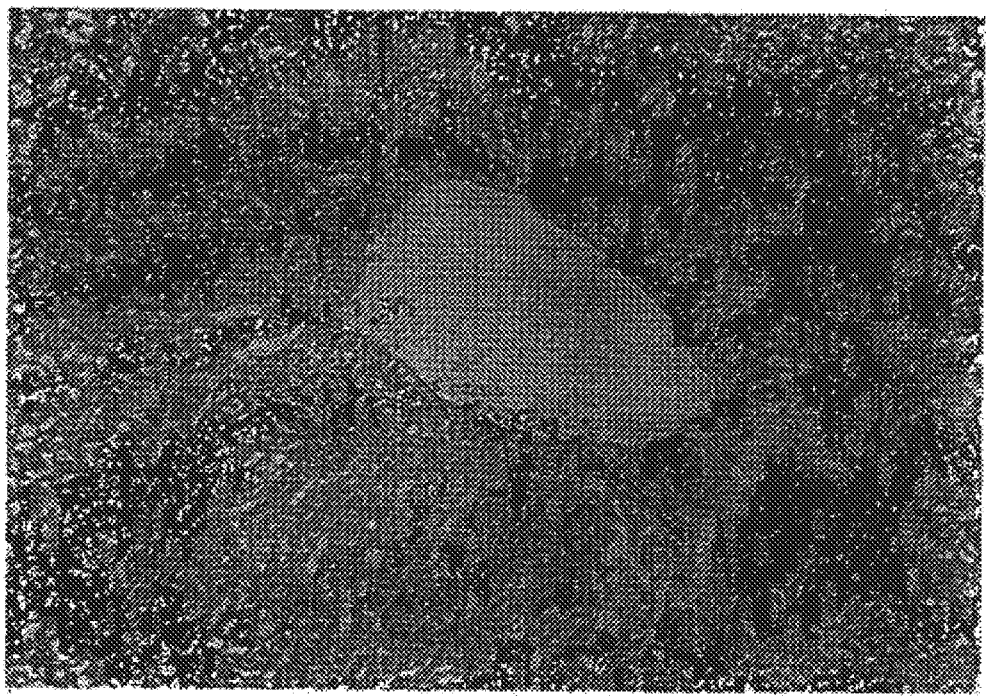
FIG. 19A: liver, ×400.
Figure 19B:
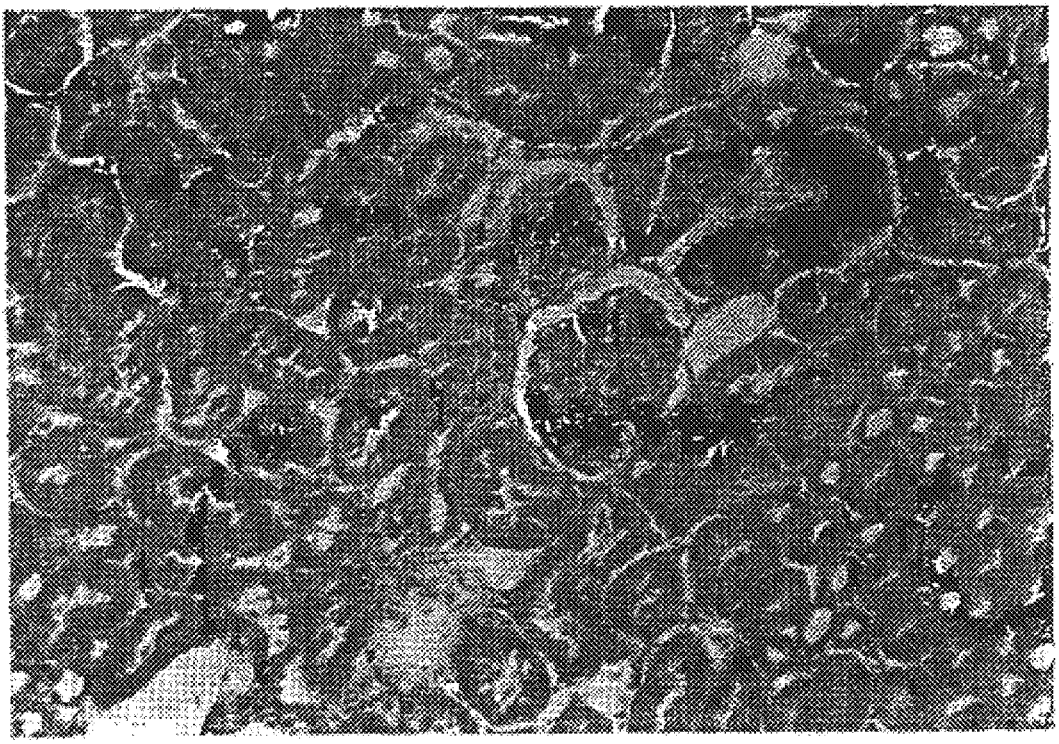
FIG. 19B: kidney, ×200.
Figure 19C:
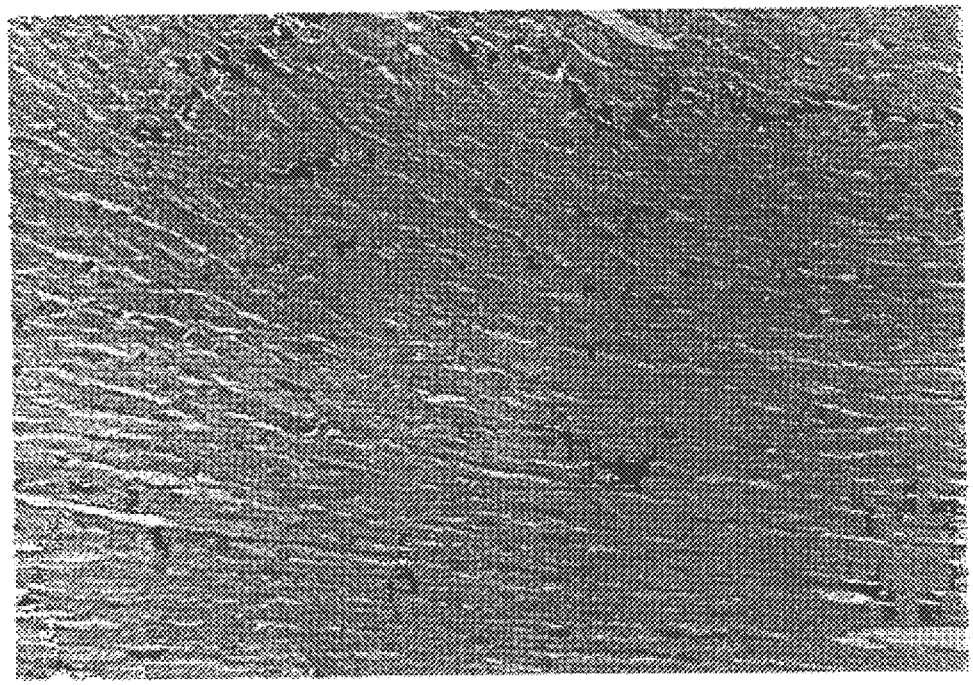
FIG. 19C: heart, ×200]

The pathohistological observation of the dissected organs of all the experimental animals in each group examined by microscope is shown in FIG. 19. Specifically, any abnormality in liver tissues due to the administration of the mixed aqueous extract of *Phellodendron amurense* RUPRECHT cortex and *Patrinia scabiosaefolia* FISCH. according to the present invention was not found, even in mice to which the mixed aqueous extract is administered via oral route in an amount of 15 g per kg of body weight (FIG. 19A). In addition, kidney did not show any abnormality due to drug administration (FIG. 19B) and myocardial cells did not show any abnormality as well (FIG. 19C). Other major organs including gastrointestinal tract, pancreas, spleen, adrenal gland, brain, testis, ovary, bone marrow, etc. did not show any abnormalities.

Therefore, it could be concluded that the mixed aqueous extract of *Phellodendron amurense* RUPRECHT cortex and *Patrinia scabiosaefolia* FISCH. according to the present invention has no side effects of acute toxicity in all organs, even at the administration of 15 g per kg of body weight (the maximum dosage which can be administered to mouse), and does not induce toxicity nor organ damages, to render its safety.

What is claimed is:

1. An aqueous extract of *Phellodendron amurense* RUPRECHT cortex and *Patrinia scabiosaefolia* FISCH wherein said extract is produced by a method comprising:

grinding a dry mixture of *Phellodendron amurense* RUPRECHT cortex and *Patrinia scabiosaefolia* FISCH;

heating and extracting said mixture with water and filtering to form a filtrate;

extracting said filtrate with an organic solvent and separating the extraction mixture into an organic and an aqueous layer; and collecting and lyophilizing said aqueous layer to obtain an aqueous extract.

2. An extract according to claim 1, wherein said dry mixture of *Phellodendron amurense* RUPRECHT cortex and *Patrinia scabiosaefolia* FISCH is in a ratio from 1:0.1 to 1:5.

3. An alcoholic extract of *Phellodendron amurense* RUPRECHT cortex and *Patrinia scabiosaefolia* FISCH wherein said extract is produced by a method comprising:

grinding a dry mixture of *Phellodendron amurense* RUPRECHT cortex and *Patrinia scabiosaefolia* FISCH;

extracting said mixture with an alcohol to produce an alcoholic extract;

cooling said alcoholic extract and evaporating said alcohol to produce a residual alcoholic extract;

adding water to said residual alcoholic extract to produce a mixture;

boiling and filtering said mixture to form a filtrate;

extracting said filtrate with an organic solvent and separating the extraction mixture into an organic and an aqueous layer; and collecting and lyophilizing said aqueous layer to obtain an alcoholic extract.

4. An extract according to claim 3, wherein said alcohol is used in a ratio of 5–40 parts by weight with respect to one part by weight of plant materials.

5. A pharmaceutical composition comprising the extract according to claim 1, and a pharmaceutically acceptable carrier.

6. A pharmaceutical composition comprising the extract according to claim 3, and a pharmaceutically acceptable carrier.

7. An extract according to claim 1, wherein said aqueous extract comprises alkaloids in the amount of about 4%.

8. An extract according to claim 7, wherein said alkaloids comprise berberine and palmitine.

9. An extract according to claim 1, wherein said aqueous extract comprises organic acids in the amount of about 3%.

10. An extract according to claim 9, wherein said organic acids are a mixture comprising benzoic acid glycoside, ferulic acid glycoside, caffeic acid glycoside, 3,4-dihydroxy benzoic acid.

11. An extract according to claim 3, wherein said alcoholic extract comprises organic acids in the amount of about 3%.

12. An extract according to claim 4, wherein said alcoholic extract comprises organic acids in the amount of about 3%.

13. A method for treating hepatitis C, comprising administering a therapeutic amount of the extract according to claim 1 to a subject requiring treatment of hepatitis C.

14. The method according to claim 13, wherein said extract is administered in a dose of 5 to 50 mg per 1 kg of body weight.

15. A method for treating hepatitis C, comprising administering a therapeutic amount of the extract according to claim 3 to a subject requiring treatment of hepatitis C.

16. The method according to claim 15, wherein said extract is administered in a dose of 5 to 50 mg per 1 kg of body weight.

17. A method for administering a therapeutic amount of a pharmaceutical composition according to claim 5.

18. The method according to claim 17, wherein said extract is administered in a dose of 5 to 50 mg per 1 kg of body weight.

19. A method for administering a therapeutic amount of a pharmaceutical composition according to claim 16.

20. The method according to claim 19, wherein said extract is administered in a dose of 5 to 50 mg per 1 kg of body weight.

* * * * *